United States Patent [19]

Kretzschmar et al.

[11] Patent Number: 5,011,827
[45] Date of Patent: Apr. 30, 1991

[54] ELAIOPHYLINE DERIVATIVES, COMPOSITIONS CONTAINING THEM AND THE USE THEREOF AS ANTHELMINTIC AGENTS

[75] Inventors: Gerhard Kretzschmar, Bad Soden am Taunus; Dieter Düwel, Hofheim am Taunus; Susanne Grabley, Königstein/Taunus; Peter Hammann, Kelkheim; Gerhard Seibert, Darmstadt; Hartmut Voelskow, Hattersheim am Main; Carlo Giani, Frankfurt am Main, all of Fed. Rep. of Germany

[73] Assignee: Hoechst Aktiengesellschaft, Frankfurt am Main, Fed. Rep. of Germany

[21] Appl. No.: 263,753

[22] Filed: Oct. 28, 1988

[30] Foreign Application Priority Data

Oct. 31, 1987 [DE] Fed. Rep. of Germany ....... 3736960

[51] Int. Cl.$^5$ ..................... A61K 31/70; C07H 17/08
[52] U.S. Cl. ..................... 514/32; 536/7.1; 514/27
[58] Field of Search ..................... 536/7.1; 514/27, 32

[56] References Cited

FOREIGN PATENT DOCUMENTS 0297523 6/1988 European Pat. Off. .
324820A1 7/1984 Fed. Rep. of Germany .
1036295 2/1986 Japan ..................... 536/7.1

OTHER PUBLICATIONS

Kaiser et al., Helv. Chim. Acta, 64(41):407-424 (1981).
Susumu et al., Chem. Abs., 106:67626 (1987).

*Primary Examiner*—Elli Peselev
*Attorney, Agent, or Firm*—Finnegan, Henderson, Farabow, Garrett, and Dunner

[57] ABSTRACT

The invention relates to elaiophyline derivatives of the formula I

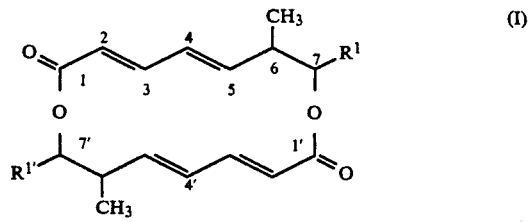

in which $R^1$ and $R^{1'}$ are identical or different and represent a radical of the formula II/or III

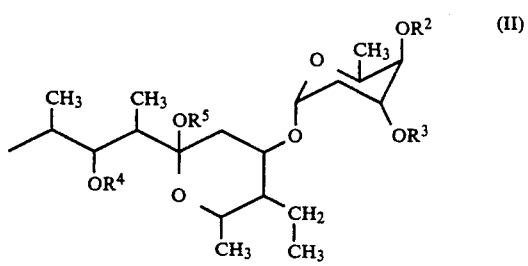

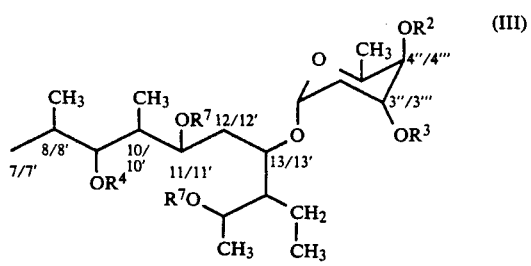

in which $R^2$, $R^3$, $R^4$, $R^5$ and $R^7$ have the meanings given. The invention furthermore relates to a process for the preparation of these elaiophyline derivatives and also the use of the lattere as medicaments, in particular as anthelmintically acting medicaments.

9 Claims, No Drawings

ELAIOPHYLINE DERIVATIVES, COMPOSITIONS CONTAINING THEM AND THE USE THEREOF AS ANTHELMINTIC AGENTS

DESCRIPTION

Elaiophyline was first isolated over 25 years ago by Arcamone et al. (giorn. Microbiol. 7, 207, 1959) and later described by Arai under the name Azalomycin B. Kaiser et al. (Helv. Chim. Acta, 64 (1981), 407) isolated elaiophyline together with nigericin and the niphitricines A and B from cultures of a strain of Streptomyces violaceoniger.

It has already been proposed (P 3,721,722.4) to employ elaiophyline as an anthelmintic, since in particular it displays a good action against gastrointestinal tract strongylidae and lung worms, with which, above all, household animals and productive animals are infested.

It has now been found that by chemical derivatization of elaiophyline the anthelmintic action can still be increased.

Several derivatives of elaiophyline are already known; however their pharmacological spectrum of action is far from the anthelmintic action described here; these derivatives are mostly employed as ulcer therapeutics.

Several alkyl, alkenyl and alkynyl derivatives and also phenyl and furylalkyl derivatives in the 11- and 11′-position of elaiophyline are already known (Japanese Preliminary Published Application 61-36295, YOKURA et al.). The reduced and partly reduced semiacetals of elaiophyline are also known, where the 6′-ring is opened at C11 or at C11 and C11′ and also the tetraacetyl derivatives (3″, 3‴, 4″, 4‴-tetra-0-acetyl) of elaiophyline (see loc. cit. Kaiser et al.). Both from the reduced semiacetals and also from the tetraacetyl derivatives, the compounds are already known in which the C—C double bonds of the macroiolide ring are completely hydrogenated (see Loc. cit. Kaier et al.).

The invention now relates to:
Elaiophyline derivatives of the formula I where the C—C double bonds in the macrodiolide ring of the compound of the formula (I) can also be hydrogenated and in which
$R^1$ is a radical of the formula II or III in which
$R^2$ and $R^3$ are identical or different and denote hydrogen or a radical of the formula IV or IV′

$$-\overset{O}{\underset{}{C}}-R^6 \quad -\overset{O}{\underset{}{C}}-(CH_2)_n-R^6$$
(IV) (IV′)

in which
n denotes 1 to 3 and
$R^6$ denotes $C_1$-$C_{15}$-alkyl, $C_2$-$C_{15}$-alkenyl, C2-C15-alkynyl, $C_3$-$C_9$-cycloalkyl, aryl or heteroaryl, where the aryl and heteroaryl radicals are optionally substituted by halogen, nitro, cyano, hydroxyl, $C_1$-$C_4$-alkyl or $C_1$-$C_4$-alkoxy and where for the case in which $R^3$ is hydrogen, $R^2$ is also hydrogen,
or in which
$R^2$ and $R^3$ are identical and denote $C_1$-$C_4$-alkyl, benzyl, allyl, MEM, MOM, SEM, trimethylsilyl, triethylsilyl, dimethylphenylsilyl, dimethylcyclohexylsilyl or dimethyl tertiary butylsilyl
or
$R^2$ and $R^3$ denote sulfonates of the formula $SO_2R^{10}$
in which $R^{10}$ denotes $C_1$-$C_{10}$-alkyl, phenyl or p-tolyl
or
$R^2$ and $R^3$ represent a radical of the formula V or V′

$$-\overset{X}{\underset{}{C}}-Z-R^{12} \quad -\overset{X}{\underset{}{C}}-Z-(CH_2)_n-R^{12}$$
(V) (V′)

in which
n denotes 1 to 3
X denotes oxygen or sulfur
$R^{12}$ denotes $C_1$-$C_{15}$-alkyl, $C_3$-$C_9$-cycloalkyl, aryl, pyridyl, pyrimidyl or pyrazinyl, where the aryl, pyridyl, pyrimidyl or pyrazinyl radicals are optionally substituted by halogen, nitro, cyano or $C_1$-$C_4$-alkoxy and
Z denotes oxygen, —N—H or a radical —N—$R^{12}$ or —N—$(CH_2)_n$—$R^{12}$, where n and $R^{12}$ have the above-mentioned meanings
or in which $R^2$ and $R^3$ together represent a radical of the formula VI in which
$R^8$ and $R^9$ are identical or different and denote hydrogen or unbranched $C_1$-$C_{10}$-alkyl or where R⁸ and R⁹ represent an alkylene chain, which together with the carbon atom carrying it, forms a 5-, 6- or 7-membered ring or in which R² and R³, for the case in which R¹ is a radical of the formula II, are identical and represent a radical of the formula VIII

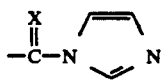 (VIII)

in which
X denotes oxygen or sulfur
or
R² and R³, for the case in which R¹ is a radical of the formula II, together represent a radical of the formula

wherein
X denotes oxygen or sulfur
and in which
R⁴, provided that R² and R³ are hydrogen, denotes hydrogen or, for the case in which R² and R³ do not denote hydrogen, is hydrogen or a radical of the formula IV or IV'

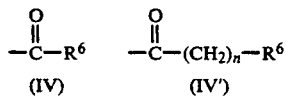

in which
n and R⁶ have the abovementioned meanings
and
R⁵ is hydrogen or a radical of the formula —$(CH_2)_n$-R⁶
where
n and R⁶ have the abovementioned meanings
and in which
R⁷ denotes hydrogen or—provided that R², R³ and R⁴ do not simultaneously denote hydrogen—forms a radical of the formula IV or IV'—as defined above
and in which
R¹' has the same meaning as R¹, where the two radicals R¹ and R¹' can be substituted both by identical —except for the radicals R⁴ and R⁵ and for the case in which R² and R³ together form a radical of the formula VI—and different substituents, with the exception that when R¹ is a radical of the formula II.in which R² and R³ form a radical of the formula VIII or in which R² and R³ together form a radical of the formula

for R¹' the radicals R² and R³ in the radical of the formula II or III are not simultaneously hydrogen, excluding elaiophyline itself, elaiophyline having a hydrogenated macrodiolide ring, and also compounds of the formula I, wherein the macrodiolide ring is hydrogenated or unhydrogenated and in which R¹ and R¹' are identical or different and represent a radical of the formula II and/or III, wherein R² and R³ denote hydrogen or acetyl and R⁴ and R⁵ or R⁷ denote hydrogen and likewise also excluding the compounds of the formula I in which the macrodiolide ring is unhydrogenated and wherein R¹ and R¹' simultaneously represent a radical of the formula II, wherein R², R³ and R⁴ denote hydrogen and wherein R⁵ denotes $C_1$-, $C_2$-, $C_4$-$C_8$, $C_{10}$-or $C_{12}$-alkyl, phenyl $C_1$-$C_3$-alkyl, para-methoxy-phenyl-methyl, cyclohexylmethyl, $C_4$-alkenyl or $C_3$-alkynyl.

The invention relates in particular to elaiophyline derivatives of the formula I, where the C–C double bonds in the macrodiolide ring of the compound of the formula I can also be hydrogenated and in which R¹ is a radical of the formula II or III, in which
R² and R³ are identical or different and denote hydrogen or a radical of the formula IV or IV'
in which
n denotes 1 to 3 and
R⁶ denotes $C_1$-$C_5$-alkyl, $C_2$-$C_5$-alkenyl, $C_2$-$C_6$ alkynyl, $C_3$-$C_6$-cycloalkyl, phenyl or furyl or thienyl, where the phenyl, furyl and thienyl radicals are optionally substituted by halogen, nitro, cyano, hydroxyl, $C_1$-$C_4$-alkyl or $C_1$-$C_4$-alkoxy and where, for the case in which R³ is hydrogen, R² is also hydrogen,
or in which
R² and R³ are identical and denote MEM, MOM, SEM, trimethylsilyl, triethylsilyl, dimethylphenylsilyl, dimethylcyclohexylsilyl or dimethyl tertiary butylsilyl
or
R² and R³ denote sulfonates of the formula $SO_2R^{10}$,
in which
R¹⁰ denotes $C_1$-$C_4$-alkyl, phenyl or p-tolyl
or
R² and R³ represent a radical of the formula V or V'
in which
n denotes 1,
X denotes oxygen,
R¹² denotes $C_1$-$C_4$-alkyl, $C_3$-$C_6$-cycloalkyl or aryl, where the aryl radical is optionally substituted by halogen, nitro, cyano or $C_1$-$C_4$-alkoxy and
Z denotes oxygen or —N—H or in which
R² and R³ together represent a radical of the formula VI
in which
R⁸ and R⁹ are identical or different and denote hydrogen or unbranched $C_1$-$C_4$-alkyl or where
R⁸ and R⁹ represent an alkylene chain which, together with the carbon atom carrying it forms a 5- or 6-membered ring
or in which
R² and R³, for the case in which R¹ is a radical of the formula II, are identical and represent a radical of the formula VIII,
in which
X denotes oxygen
or
R² and R³, for the case in which R¹ is a radical of the formula II, together represent a radical of the formula

in which
X denotes oxygen
and in which
$R^4$, provided $R^2$ and $R^3$ are hydrogen, denotes hydrogen or, for the case in which $R^2$ and $R^3$ do not denote hydrogen, is hydrogen or a radical of the formula IV or IV',
in which
n is 1 to 3 and $R^6$ has the abovementioned meanings, and
$R^5$ is hydrogen or a radical of the formula —$(CH_2)_n$—$R^6$
where
n is 1 to 3 and $R^6$ has the abovementioned meanings
and in which
$R^7$ denotes hydrogen or—provided $R^2$, $R^3$ and $R^4$ do not simultaneously denote hydrogen—forms a radical of the formula IV or IV' as defined above
and in which
$R^{1'}$ has the same meaning as $R^1$, in which the two radicals $R^1$ and $R^{1'}$ can be substituted both by identical substituents and also—except for the radicals $R^4$ and $R^5$ and for the case in which $R^2$ and $R^3$ together form a radical of the formula VI—different substituents, with the exception that when $R^1$ is a radical of the formula II in which $R^2$ and $R^3$ form a radical of the formula VIII or in which $R^2$ and $R^3$ together form a radical of the formula

for $R^{1'}$ the radicals $R^2$ and $R^3$ in the radical of the formula II or III are not simultaneously hydrogen,
excluding elaiophyline itself, elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II and/or III, in which $R^2$ and $R^3$ denote hydrogen or acetyl and $R^4$ and $R^5$ or $R^7$ denote hydrogen and likewise also excluding the compounds of the formula I, in which the macrodiolide ring is unhydrogenated and in which $R^1$ and $R^{1'}$ simultaneously represent a radical of the formula II, in which $R^2$, $R^3$ and $R^4$ denote hydrogen and in which
$R^5$ denotes $C_1$-, $C_2$-, $C_4$-$C_5$-alkyl, phenyl-$C_1$-$C_3$-alkyl, para-methoxy-phenyl-methyl, cyclohexylmethyl, $C_4$-alkenyl or $C_3$-alkynyl.

Elaiophyline derivatives of the formula I are particularly preferred where the C—C double bonds in the macrodiolide ring of the compound of the formula I can also be hydrogenated and in which $R^1$ is a radical of the formula II or III, in which
$R^2$ and $R^3$ are identical or different and denote hydrogen or a radical of the formula IV or IV', in which
n denotes 1,
$R^6$ denotes $C_1$-$C_5$-alkyl, cyclohexyl, phenyl, furyl or thienyl, in which the phenyl, furyl, and thienyl radicals are optionally substituted with fluorine, chlorine or bromine and where, for the case in which $R^3$ is hydrogen, $R^2$ is also hydrogen,
or in which
$R^2$ and $R^3$ are identical and denote MEM, MOM, SEM, trimethylsilyl, triethylsilyl, dimethylphenylsilyl, dimethylcyclohexylsilyl or dimethyl tertiary butylsilyl
or
$R^2$ and $R^3$ denote sulfonates of the formula $SO_2R^{10}$
in which
$R^{10}$ denotes methyl, phenyl or p-tolyl
or
$R^2$ and $R^3$ represent a radical of the formula V or V',
in which
n denotes 1
X denotes oxygen
$R^{12}$ denotes cyclohexyl or aryl, where the aryl radical is optionally substituted by halogen, nitro, cyano or $C_1$-$C_4$-alkoxy and
Z denotes oxygen or -N-H,
or in which
H $R^2$ and $R^3$ together represent a radical of the formula VI
in which
$R^8$ and $R^9$ are identical or different and denote hydrogen or unbranched $C_1$-$C_4$-alkyl or where
$R^8$ and $R^9$ represent an alkylene chain which, together with the carbon atom carrying it forms a 5- or 6-membered ring
or in which
$R^2$ and $R^3$, for the case in which $R^1$ is a radical of the formula II, are identical and represent a radical of the formula VIII
in which
X denotes oxygen
or
$R^2$ and $R^3$, for the case in which $R^1$ is a radical of the formula II, together represent a radical of the formula

in which
X denotes oxygen
and in which
$R^4$, provided $R^2$ and $R^3$ are hydrogen, denotes hydrogen or, for the case in which $R^2$ and $R^3$ do not denote hydrogen, is hydrogen or a radical of the formula IV or IV',
n is 1 and $R^6$ has the abovementioned meanings
and
$R^5$ is hydrogen or a radical of the formula -$(CH_2)_n$-$R^6$
in which
n is 1 and $R^6$ has the abovementioned meanings and in which
$R^7$ denotes hydrogen or—provided R2, $R^3$ and $R^4$ do not simultaneously denote hydrogen—forms a radical of the formula IV or IV'—as defined above—
and in which
$R^{1'}$ has the same meaning as $R^1$, where the two radicals $R^1$ and $R^{1'}$ can be substituted both with identical substituents and also—except for the radicals $R^4$ and $R^5$ and for the case in which $R^2$ and $R^3$ together form a radical of the formula VI—and likewise also different substituents, with the exception that when $R^1$ is a radical of the formula II, in which $R^2$ and $R^3$ form a radical of the formula VIII or in which $R^2$ and $R^3$ together form a radical of the formula

for $R^{1'}$ the radicals $R^2$ and $R^3$ in the radical of the formula II or III are not simultaneously hydrogen, excluding elaiophyline itsself, elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II and/or III, in which $R^2$ and $R^3$ denote hydrogen or acetyl and $R^4$ and $R^5$ or $R^7$ denote hydrogen and likewise also excluding the compounds of the formula I in which the macrodiolide ring is not hydrogenated and in which $R^1$ and $R^{1'}$ simultaneously represent a radical of the formula II, in which $R^2$, $R^3$ and $R^4$ denote hydrogen and in which $R^5$ denotes $C_1$-$C_2$- or $C_4$-$C_5$-alkyl, phenylmethyl or cyclohexylmethyl.

The invention furthermore relates to elaiophyline derivatives of the formula I as claimed in claim 1, but including elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II and/or III, in which $R^2$ and $R^3$ denote hydrogen or acetyl and $R^4$ and $R^5$ or $R^7$ denote hydrogen and likewise also including the compounds of the formula I, in which the macrodiolide ring is not hydrogenated and in which $R^1$ and $R^{1'}$ simultaneously represent a radical of the formula II, in which $R^2$, $R^3$ and $R^4$ denote hydrogen and in which $R^5$ denotes $C_1$-, $C_2$-, $C_4$-$C_8$, $C_{10}$- or $C_{12}$-alkyl, phenylR $C_1$-$C_3$-alkyl, para-methoxy-phenyl-methyl, cyclohexylmethyl, $C_4$-alkenyl or $C_3$-alkynyl, for use as anthelmintics.

Preferred elaiophyline derivatives are those of the formula I, as claimed in claim 2, but including elaiophyline having a hydrogenated macrodiolide ring, and also compounds of the formula I in which the macrodiolide ring is hydrogenated or unhydrogenated and in which $R^1$ and $R^{1'}$ are identical or different and represent a radical of the formula II and/or III, in which $R^2$ and $R^3$ denote hydrogen or acetyl and $R^4$ and $R^5$ or $R^7$ denote hydrogen and likewise also including the compounds of the formula I in which the macrodiolide ring is not hydrogenated and in which $R^1$ and $R^{1'}$ simultaneously represent a radical of the formula II, in which $R^2$, $R^3$ and $R^4$ denote hydrogen and in which $R^5$ denotes $C_1$-, $C_2$-, $C_4$-$C_5$-alkyl, phenyl-$C_1$-$C_3$-alkyl, para-methoxy-phenyl-methyl, cyclohexylmethyl, $C_4$-alkenyl or $C_3$-alkynyl, for use as anthelmintics.

Particularly preferred elaiophyline derivatives are those of the formula 1, as claimed in claim 3, but including elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II and/or III, in which $R^2$ and $R^3$ denote hydrogen or acetyl and $R^4$ and $R^5$ or $R^7$ denotes hydrogen and likewise also including the compounds of the formula I, in which the macrodiolide ring is not hydrogenated and in which $R^1$ and $R^{1'}$ simultaneously represent a radical of the.formula II, in which $R^2$, $R^3$ and $R^4$ denote hydrogen and in which $R^5$ denotes $C_1$-$C_2$-, $C_4$-$C_5$-alkyl, phenylmethyl or cyclohexylmethyl, for use as anthelmintics.

The invention likewise relates to a process for the preparation of elaiophyline derivatives of the formula I wherein (a) elaiophyline (formula I: $R^1=R^{1'}=$II, $R^2=R^3=R^4=R^5=$H) or a compound of the formula I in which $R^1$ and $R^{1'}$ are identical or different and represent a radical of the formula II and/or III, in which $R^2$, $R^3$ and $R^4$ have the abovementioned meanings and $R^5$ or $R^7$, except for hydrogen, have the abovementioned meanings, is reacted with a compound of the formula IX or IX'.

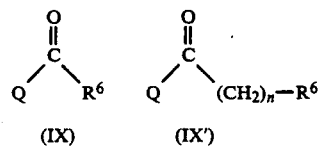

in which n and $R^6$ have the meanings mentioned above for formula IV or IV' and Q denotes chloride, bromide, an imidazolide or an acid anhydride, by means of which compounds of the formula I are obtained, in which $R^1$ and $R^{1'}$ are identical or different and represent a radical of the formula II and/or III, in which $R^2$ and $R^3$ are identical or different and represent a radical of the formula IV or IV', as defined above, and in which $R^4$ and $R^5$ or $R^7$ remain unchanged compared to the starting compound, or wherein (b) an elaiophyline derivative of the formula I in which $R^1$ and $R^{1'}$ are identical or different and represent a radical of the formula II and/or III, in which $R^2$, $R^3$ and $R^4$ have the abovementioned meanings and $R^5$ or $R^7$, except for hydrogen, have the abovementioned meanings, are reacted with a compound selected from: $C_1$-$C_4$-alkyl, benzyl, or allyl chloride, bromide or iodide, or MEM chloride, MOM chloride or SEM chloride, trimethylsilyl-, triethylsilyl-, dimethylphenylsilyl-, dimethylcyclohexylsilyl- or dimethyl tertiary butylsilyl chloride, sulfonyl halides of the formula Y—$SO_2R^{10}$, in which Y denotes chlorine, bromine or iodine and $R^{10}$ has the abovementioned meanings, isocyanates of the formula

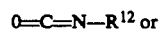

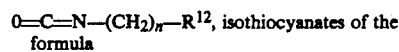

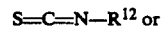

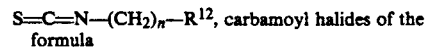

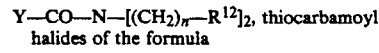

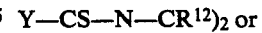

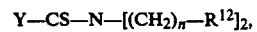

where n and $R^{12}$ have the meanings given above for formula V or V' and Y denotes chlorine or bromine, by means of which compounds of the formula I are obtained, in which $R^1$ and $R^{1'}$ are identical or different and represent a radical of the formula II and/or III, in which $R^2$ and $R^3$ are identical and represent a $C_1$-$C_4$alkyl, benzyl, allyl, MEM, MOM, SEM, trimethylsilyl, triethylsilyl, dimethylphenylsilyl, dimethylcyclohexylsilyl or dimethyl tertiary butylsilyl radical or a sulfonate of the formula $SO_2R^{10}$ or a radical of the formula V or V', where $R^{10}$ and the formulae V and V' have the abovementioned meanings and in which $R^4$ and $R^5$ or $R^7$ are unchanged compared to the starting compound, or wherein (c) elaiophyline (formula I: $R^1=R^{1'}=$II, $R^2=R^3=R^4=R^5=$H) is reacted with an aldehyde/ketone of the formula X

or with a ketal of the formula XI

in which denotes methyl or ethyl and $R^8$ and $R^9$ have the abovementioned meanings, by means of which compounds of the formula I are obtained, in which $R^1$ and $R^{1'}$ are identical and represent a radical of the formula II, in which $R^2$ and $R^3$ together represent a radical of the formula VI, as defined above, or wherein (d) elaiophyline (formula I: $R^1=R^{1'}=$II, $R^2=R^3=R^4=R^5=$H) or a compound of the formula I, in which $R^1$ and $R^{1'}$ are identical or different and represent a radical of the formula II, in which $R^2$, $R^3$ and $R^4$ have the abovementioned meanings and $R^5$, except for hydrogen, has the abovementioned meanings, are reacted if appropriate in the presence of a base with carbonyldiimidazole or thiocarbonyldiimidazole, by means of which compounds of the formula I are obtained, in which $R^1$ and $R^{1'}$ are identical or different and represent a radical of the formula II, in which $R^2$ and $R^3$ are identical and represent a radical of the formula VIII, as defined above, or in which $R^2$ and $R^3$ together represent a radical of the formula

as defined above, and in which $R^4$ and $R^5$ are unchanged compared to the starting compound, or wherein (e) a compound of the formula I, in which $R^1$ and $R^{1'}$ are identical or different and represent a radical of the formula II and/or III, in which $R^2$ and $R^3$, except for hydrogen, have the abovementioned meanings and in.which $R^4$ denotes hydrogen and $R^5$ or $R^7$, except for hydrogen, has the abovementioned meanings, is reacted according to process variation a) with a compound of the formula IX or IX', as defined under a), by means of which compounds of the formula I are obtained, in which $R^1$ and $R^{1'}$ are identical or different and represent a radical of the formula II and/or III, in which $R^2$ and $R^3$, except for hydrogen, have the abovementioned meanings and $R^4$ denotes a radical of the formula IV or IV', as defined above, in which $R^4$ in $R^{1'}$ is identical with $R^4$ in $R^1$ and in which $R^5$ or $R^7$ is unchanged compared to the starting compound, or wherein (f) elaiophyline or a compound of the formula I, in which $R^1$ and $R^{1'}$ are identical or different and represent a radical of the formula II, in which $R^2$, $R^3$ and $R^4$ have the abovementioned meanings and in which $R^5$ denotes hydrogen, is preferably reacted in the presence of a Lewis acid with an alcohol of the formula HO-$(CH_2)$n-$R^6$ in which n and $R^6$ have the abovementioned meanings, by means cf which compounds of the formula I are obtained, in which $R^1$ and $R^{1'}$ are identical or different and represent a radical of the formula II, in which $R^2$ and $R^3$ and $R^4$ have the abovementioned meanings and $R^5$ in the radicals $R^1$ and $R^{1'}$ is identical and represents a radical of the formula—$(CH_2)_n$—$R^6$ or —$R^6$, as defined above, or wherein (g) elaiophyline (formula I: $R^1=R^{1'}=$II, $R^2=R^3=R^4=R^5=$H) or a compound of the formula I in which $R^1$ and $R^{1'}$ are identical or different and represent a radical of the formula II, wherein $R^2$, $R^3$ and $R^4$ have the abovementioned meanings and $R^5$ is hydrogen, where the substituents of the formula VIII and also the carbonyl and thiocarbonyl radicals are excluded for $R^2$ and $R^3$, is reduced, by means of which a compound of the formula I is obtained, in which $R^1$ and/or $R^{1'}$ is a radical of the formula III, in which $R^2$, $R^3$ and $R^4$ have the abovementioned meanings and $R^7$ denotes hydrogen, or wherein (h) a compound of the formula I, in which $R^1$ and/or $R^{1'}$ is a radical of the formula III in which $R^2$ $R^3$ and $R^4$ have the abovementioned meanings and $R^7$ denotes hydrogen, is reacted according to process variation (a) with a compound of the formula IX or IX', as defined in process variation a), to give a compound of the formula I, in which $R^1$ and/or $R^{1'}$ is a radical of the formula III, in which $R^2$, $R^3$ and $R^4$ have the abovementioned meanings or, provided that $R^2$ and/or $R^3$ and/or $R^4$ denoted hydrogen before the reaction, $R^2$ and/or $R^3$ and/or $R^4$ after the reaction have the meaning of $R^7$, and in which $R^7$ is a radical of the formula IV or IV', as defined above, or wherein (i) a compound of the formula I, in which $R^1$ and/or $R^{1'}$ is a radical of the formula II and/or III, in which $R^2$, $R^3$, $R^4$ and $R^5$ or $R^7$ have the abovementioned meanings, is hydrogenated, by means of which a hydrogenated com pound of the formula I is obtained, in which $R^1$ and/or $R^{1'}$ is a radical of the formula II and/or III, in which $R^2$, $R^3$, $R^4$ and $R^5$ or $R^7$ have the abovementioned meanings.

Aryl is taken to mean aromatic hydrocarbons, in particular phenyl and naphthyl and heteroaryl is taken to mean heteroaromatic hydrocarbons, in particular thiophene and furan, but also pyridine, pyrimidine and pyrazine.

Halogens are taken to mean fluorine, chlorine, bromine and iodine, MEM is taken to mean methoxyethoxymethyl, MOM is taken to mean methoxymethyl and SEM is taken to mean $\beta$-trimethylsilylethoxymethyl.

The macrodiolide ring of elaiophyline can—independently of the type of substituents $R^1$ and $R^{1'}$—be hydrogenated or unhydrogenated.

The substituents $R^1$ and $R^{1'}$ can be both identical and different, i.e. it is possible both that $R^1$ and $R^{1'}$ represent a radical of the formula II or III and also that $R^1$ represents a radical of the formula II and $R^{1'}$ represents a radical of the formula III (the reverse: $R^1$=a radical of the formula III and $R^{1'}$=a radical of the formula II is, based on the symmetry of the molecule, identical with $R^1$=II and $R^{1'}$=III). Likewise it is possible—with H a few exceptions - to build different $R^2$, $R^3$, $R^4$, $R^5$ or $R^7$ radicals into the radicals $R^1$ and $R^{1'}$. This is independent of whether the radicals $R^1$ and $R^{1'}$ now both represent a radical of the formula II or III or are different, i.e. $R^1$ represents a radical of the formula II and $R^{1'}$ represents a radical of the formula III. However, if $R^1$ and $R^{1'}$ represent a radical of the formula II, then $R^5$ is the same in both substituents $R^1$ and $R^{1'}$ The substituent $R^4$ is always identical in the radicals $R^1$ and $R^{1'}$ and can then only be different from hydrogen when the substituents $R^2$ and $R^3$ are also different from hydrogen. Likewise, $R^2$ can then only be different from hydrogen when $R^3$ is also different from hydrogen.

In the following, the processes (a) to (h), which make it possible to prepare the different substituted elaiophyline derivatives, are more closely described.

With the aid of process variation a), the hydroxyl groups in the 3"—or 3""—position and 4"—or 4"'—position of elaiophyline can be esterified. Since the reaction rate of the esterification in the 3"—or 3"'—position —i.e. for the $R^3$ derivative—is greater than that of the esterification in the 4"—or 4"'—position, the possibility presents itself to provide both identical and also different substituents for $R^2$ and $R^3$. Likewise, it is possible in this manner to build different $R^2$ and/or $R^3$ radicals into the substituents $R^1$ and $R^{1'}$. For example, elaiophyline—or its homologue having a hydrogenated macrodiolide ring—can be monoacetylated with a reagent A (for example in the 3"—position) and then converted with a reagent B—into a 3"', 4", 4"'—tri-0-acetyl(B)—3"-0-acetyl(A)-derivative. In a similar manner, it is completely possible to introduce four different substituents into the 3"-, 3"'-, 4"- and 4"'-position in the molecule.

At relatively high temperatures and/or sufficiently long reaction times, the OH group in the 9- or 9'-position is also esterified. This, however, also denotes that an esterification in the 9- or 9'-position is only possible after previous esterification of the OH groups in the 3"/3"'- and 4"/4"'-position. In this manner, for example, the OH groups in the 3"/3"'- and 4"/4"'-position can therefore be initially esterified and then, if appropriate after isolating and purifying the product, the OH group in the 9- and/or 9'-position can then be esterified in a second reaction (process variation e) corresponding to process variation a.

In process variation a), a procedure is thus best used in which elaiophyline ($R^1=R^{1'}=II$; $R^2$, $R^3$, $R^4$ or $R^5=H$) or a compound of the formula I, in which $R^1$ and $R1'$ are identical or different and represent a radical of the formula II and/or III, in which $R2$, $R^3$ and $R^4$ have the abovementioned meanings and $R^5$ or R7, except for hydrogen, have the abovementioned meanings, is reacted in equimolar amounts or in up to a 50-fold excess, if appropriate in an inert, aprotic solvent such as chloroform, methylene chloride, tetrahydrofuran (THF), ethyl acetate or dioxane, with a compound of the formula IX or IX' until completion of the reaction, if appropriate in the presence of a base, preferably pyridine.

The reaction temperatures in this case lie between $-70°$ C. and $+100°$ C., preferably when using a solvent between the solidification point and the boiling point of the solvent, in particular between $-70°$ C. and $+40°$ C. The reaction times are 1 to 180 hours, preferably 1 to 48 hours, particularly preferably 1 to 8 hours. The completion of the reaction can be determined, for example, by means of thin layer chromatography (TLC checking).

The elaiophyline required as the starting substance can be prepared, for example, according to the process described in the German Patent Application P 3,721,722.4. Here, elaiophyline is produced as the fermentation product of cultures of the strains Streptomyces violaceoniger DSM 4137 or Streptomyces parvulus DSM 3816.

The starting compounds for process variation a), the compounds of the formula IX and/or IX', can be prepared, unless commercially available, in a simple manner by processes known in the literature. For example, the acid chlorides are obtained by reaction of the corresponding carboxylic acid with thionyl chloride, $PCL_3$ or $PCL_5$. Such processes are, for example, described in Gattermann/Wieland, "Die Praxis des Organischen Chemikers" ("The Practice of Organic Chemists"), 43rd edition, Walter de Gruyter, Berlin, New York 1982, page 303 et seq.

In process variation (b), a procedure is thus best used in which elaiophyline or an elaiophyline derivative is reacted in equimolar amounts or in an excess of up to 50-fold with a compound which is selected from:

$C_1$-$C_4$-alkyl, benzyl or allyl chloride, bromide or iodide, or MEM chloride, MOM chloride or SEM chloride, trimethyl- silyl-, triethylsilyl-, dimethylphenylsilyl-, dimethyl- cyclohexylsilyl- or dimethyl tert.-butylsilyl chloride, H sulfonyl halides of the formula Y-$SO_2R^{10}$, isocyanates of the formula $O=2$ or $0=C=N-(CH_2)_n-R^{12}$, isothiocyanates of the formula or $S=C=N$-$(CH_2)_n$—$R^{12}$, carbamoyl halides of the formula Y-CO-N-$(R^{12})_2$ or Y-CO-N-$[(CH_2)_n$—$R^{12}]_2$, thiocarbamoyl halides of the formula Y-CS-N-$(R^{12})_2$ or Y-CS-N-$[(CH_2)_n$—$R^{12}]_2$.

If appropriate, this reaction can also take place with the addition of a base. Suitable bases are, for example, triethylamine, pyridine or lutidine. A variation of process b) consists of working in a suitable, preferably inert solvent such as chloroform, methylene chloride, THF, ethyl acetate or dioxane. The excess of the abovementioned compounds can also be up to a 50-fold amount here.

The reaction temperatures here lie between $-70°$ C. and $+100°$ C, preferably when using a solvent between the solidifying point and the boiling point of the solvent, in particular between $-70°$ C and $-40°$ C. The reaction times are to 180 hours, preferably 1 to 48 hours, particularly preferably 1 to 8 hours. The completion of the reaction can, for example, be determined by means of TLC checking.

The starting compounds for process variation b) can be prepared, unless commercially available, in a simple manner by processes known in the literature. For example, the sulfonyl halides of the formula Y-$SO_2R^{10}$ is obtained by radical reaction of alkanes with chlorine and $SO_2$ or by halogenation of aromatics with a halogenosulfonic acid Y—$SO_3H$. The isocyanates, isothiocyanates, carbamoyl halides and thiocarbamoyl halides are obtained by processes known from the literature such as are described, for example, in Houben-Weyl, 4th edition, Georg Thieme Verlag Stuttgart (1983), Volume E4.

With the aid of process variation c), the hydroxyl groups in the 3''-/3'''-position and 4''-/4'''-position of elaiophyline can be acetalated with radicals $R^2$ and $R^3$, which together represent a radical of the formula VI.

In process variation (c), a procedure is thus best used in which elaiophyline is reacted in excess with a compound of the formula X or XI until completion of the reaction, if appropriate in the presence of a Lewis acid such as $ZnCL_2$, $ZnBr_2$, $FeCL_3$, $CuSO_4$ or $CuCL_2$. A variation of process b) consists of working in a suitable, aprotic solvent such as chloroform, methylene chloride, THF, ethyl acetate or dioxane. An excess of X or XI can also be used here.

The reaction temperatures here lie between $-20°$ C and $+100°$ C, preferably when using a solvent between room temperature and the boiling point of the solvent, in particular between 20° C. and 100° C. The reaction times are 1 to 50 hours, preferably 1 to 12 hours. The completion of the reaction can be determined, for example, by means of TLC checking.

The starting compounds for process variation c), the compounds of the formula X and/or XI, can be prepared, unless commercially available, in a simple manner by processes known from the literature. For example, the aldehydes of the formula X are obtained by oxidation of primary alcohols or by reduction of carbonyl derivatives, for example with complex hydrides or by reduction of carboxyl chlorides (additional examples for the synthesis of aldehydes, ketones and acetals or ketals can be found in Organikum, Organisch Chemisches Praktikum, 15th edition, VEB Deutscher Verlag der Wissenschaften, Berlin 1976, Method Index, Acetals, Ketals, Aldehydes, Ketones, page 819 et seq.).

With the aid of process variation d), the hydroxyl groups in the 3''-/3'''-position and 4''-/4'''-position of elaiophyline can be converted into the $OR^2$-/$OR^3$- derivatives, in which $R^2$ and/or $R^3$ represents a carbonylimidazolide, thiocarbonylimidazolide or together represent a carbonyl or thiocarbonyl radical. The reaction can be controlled in which, for example, the radical $R^1$ and $R^{1'}$ are identical and the substituents $R^2$ and $R^3$ are also identical and denote carbonyl or thiocarbonylimidazole. Likewise, the reaction can, however, also be controlled in which in the radical $R^1$ the substituents $R^2$ and $R^3$ represent a carbonyl or thiocarbonyl radical and in the radical $R^{1'}$ the L substituents $R^2$ and $R^3$ are identical and denote carbonyl or thioncarbonylimidazole. This reaction can be influenced, for example, by a suitable variation of the mixing ratios of the starting substance or by the temperature control of the reaction. Thus, for example, the corresponding carbonyls or thiocarbonyls are formed from the carbonyl or thiocarbonylimidazolides in greater quantities at higher temperatures.

In process variation (d), a procedure is thus best used in which elaiophyline or an elaiophyline derivative is reacted in equimolar amounts or in an excess of up to 5-fold with carbonyldiimidazole or thiocarbonyldiimidazole until completion of the reaction, if appropriate in the presence of a base such as pyridine. A variation of the process consists of working in a suitable aprotic solvent such as chloroform, methylene chloride, THF, ethyl acetate or dioxane. An excess of carbonyldiimidazole or thiocarbonyldiimidazole, which can be up to about a 5-fold amount, can also be used here. The reaction temperatures in this case are between 0° C. and 100° C, preferably when using a solvent between the solidifying point and the boiling point of the solvent, in particular between 0° C. and 40° C. The reaction times are 1 to 48 hours, preferably 1 to 24 hours. The completion of the reaction can be determined, for example, by means of TLC checking.

The starting compounds for process variation (d), carbonyldiimidazole or thiocarbonyldiimidazole, are commercially available.

With the aid of process variation (e), the OH groups in the 9- and/or 9'-position can be esterified, as already described above. A prerequisite for an esterification in this position is that the protons of the OH-groups in the 1''-/4''—position and 3'''-/4'''-position are already substituted. Otherwise, first these OH-groups would react with the acylating reagents and only later—in a suitable excess—those in the 9-/9'-position. The substituents $R^2$ and $R^3$ could, for example, be introduced into the molecule in one of the described process variations (a) to (d). All process parameters for variation (e) are to be inferred from the description of variation (a). In some cases particularly when $R^2$/$R^3$ and $R^4$ hould represent different substituents—it is expedient, in connection with one of the process variations (a) to (d), to isolate and if necessary to purify the reaction products before it is reacted further according to process variation (e).

The required starting compounds of the formula IX and IX' are either commercially available or can be synthesized simply in the manner described for variation (a).

With process variation f), the substituent $R^5$ can be introduced into the molecule. Here, this reaction can be carried out selectively on the OH-group of the $C_{11}$-/$C_{11}'$-position, independently of the type of the substituents $R^2$, $R^3$ and $R^4$ In this process variation, a procedure is thus best used in which elaiophyline or a suitable $R^2$, $R^3$ or $R^4$ derivative is reacted with an excess of an alcohol of the formula HO-$(CH_2)_n$-$R^6$ in the presence of catalytic amounts of a Lewis acid until completion of the reaction. A variation of the process consists in working in a suitable solvent such as chloroform, methylene chloride, THF, ethyl acetate or dioxane. Suitable Lewis acids are, for example, halides of copper, iron or lithium, in particular $CuCL_2$, $FeCL_3$ or-LiBr.

The concentration of the Lewis acid—in relation to L elaiophyline or the elaiophyline derivative—is 0.1 to 5% by weight, preferably 0.5 to 1% by weight. The reaction temperatures here lie between $-40°$ C. and $+100°$ C., in particular between 0° C. and 30° C., preferably when using a solvent between the solidifying point and the boiling point of the solvent, in particular between 0° C. and 30° C. The reaction times are 1 to 180 minutes, preferably 5 to 60 minutes. The completion of the reaction can be determined, for example, by means of thin layer chromatography.

With the aid of process variation (g), the semiacetal of elaiophyline can be reduced, by means of which the 6-ring 35 is opened at $C_{11}$ or $C_{11}'$. This reduction can only be carried out, however, when $R^5$ denotes hydrogen. With the exception of the case in which $R^2$ and $R^3$ represent a carbonylimidazolide, a thiocarbonylimidazolide or together represent a carbonyl or thiocarbonyl radical, the type of the remaining substituents $R^2$, $R^3$ and $R^4$ is uncritical for the reduction.

In process variation (g), a procedure is thus best used in which elaiophyline or an elaiophyline derivative obtainable by one of the process variations a) to f) or i) is reduced using a boranate of an alkali metal or an alkaline earth metal, preferably using NaBH$_4$ in a solvent, preferably in an alcohol such as isopropanol or in an ether such as THF. Suitable methods are described, for example, in Houben-Weyl, 4th edition, Volume 4/1d, G. Thieme Verlag, Stuttgart 1981.

The reaction temperatures here lie between −70° C. and 100° C., preferably between the solidifying point and the boiling point of the solvent, in particular between −20° C. and +20° C. The reaction times are 1 to 60 hours, preferably 5 to 20 hours. The completion of the reaction can be determined, for example, by means of TLC checking.

By means of process variation h) the hydroxyl groups at C11/C11' and C15/15' can be esterified. Here, process variation a) again comes into use, which at the same time means, however, that before the esterification of the C15/C15'- and C11/ C11'-OH-groups, the OH-groups in the 3''/3'''- and 2''/2'''-position and if appropriate also those in the 9/9'-position first would have to be esterified, since otherwise these OH-groups would be esterified in one o step with the C15/15'-and C11/11'-OH-groups.

All process parameters for variation h) are to be inferred from the description of variation a). In some cases, particularly when $R^2$, $R^3$, $R^4$ and $R^7$ represent different substituents, it is expedient in connection with one or more of the process variations (a) to (e) and (g) to isolate and if necessary, to purify the reaction products before the desired product is reacted further according to process variation (h).

With the aid of process variation (i), the C-C double bonds of the macrodiolide ring can be hydrogenated. This hydrogenation can take place both before and after the reactions according to one or more of the process variations (a) to (h). Provided that the desired elaiophyline derivative contains unsaturated or reducible $R^2$, $R^3$, $R^4$, $R^5$ or $R^7$ substituents, the hydrogenation of the macrodiolide ring expediently takes place before the attachment of the corresponding unsaturated substituent(s).

In process variation (i), a procedure is thus best used in which the elaiophyline or elaiophyline derivative to be hydrogenated, preferably dissolved in a solvent such as methanol, ethanol, isopropanol or ethyl acetate, or a mixture of these solvents or an aqueous mixture of these solvents, is reacted with hydrogen in the presence of a customary hydrogenation catalyst according to processes known from the literature. Customary hydrogenation catalysts are, for example, elements of the 8th group such as 20 platinum, palladium and also nickel, which are mostly applied to activated charcoal, silica or alumina supports, for example, for the purpose of increasing the reactive surface. If the reaction is carried out in an absolute primary alcohol as the solvent, then in addition to a hydrogenation of the C=C double bonds, a ketalization to the $C_{11}/C_{11}'$-di-O-alkylene is also obtained.

According to the catalyst used, the reaction can be carried out both without and with excess hydrogen pressure, for example up to 1 atmosphere. The reaction temperatures are between 0° C. and 40° C., preferably at room temperature. The reaction times are dependent on the batch size and the concentration of the compound to be reduced. Such hydrogenation processes are described, for example, in Organikum, Organisch Chemisches Grundpraktikum, 15th edition, VEB Deutscher Verlag der Wissenschaften, Berlin, 1976, pages 359-371.

The purification, isolation and working up of the substances takes place by customary methods; for example the reaction products can be purified by chromatography on polar support materials such as silica gel or ®Sephadex LH 20 using solvents such as lower alkanols such as methanol or chloroform or ethyl acetate or methanol/chloroform mixtures, but also by extraction methods such as liquid/liquid extraction or solid/liquid extraction or by crystallization.

The derivatives of elaiophyline show anthelmintic action, in particular against Haemonchus, Trichostrongylus, Ostertagia, Cooperia, Chabertia, Strongyloides, Oesophagostomum, Hygostrongylus, Ancylostoma, Ascaris and Heterakis. The activity towards gastrointestinal tract strongylidae and lung worms, with which household and productive animals, above all, are infested, is particularly marked.

The elaiophyline derivatives can fundamentally be administered as a substance per se. Use in a mixture with a suitable carrier material is preferred. The customary feedstuff mixtures can be used as carrier materials.

The invention is further illustrated in the following examples. Percentage data relate to the weight and mixture ratios in liquids relate to the volume, when no other data have been given.

EXAMPLES

General process instructions

Process 1 mmol of macrodiolide of the elaiophyline type (this is taken to mean compounds of the formula I in which the macrodiolide ring is hydrogenated or unhydrogenated) are dissolved in 10 ml of chloroform and 10 ml of pyridine and stirred with the appropriate carboxylic acid derivatives. The excess of carboxylic acid derivative is decomposed using 50 ml of water. The product is transferred into the organic phase by extracting three times with ethyl acetate. The organic phase is washed with 0.1 N hydrochloric acid and water, dried over sodium sulfate and concentrated in vacuo. By chromatography on 100 g of silica gel using a linear gradient ethyl acetate: hexane/1:5 in ethyl acetate (about 5 liters), the corresponding compounds are obtained (see Table 1 and 2).

Process 2

1 mmol of macrodiolide of the elaiophyline type is dissolved in 10 ml of alcohol and stirred with 70 mg of FeCL$_3$ at room temperature. After the addition of 100 ml of ethyl acetate, the mixture is washed twice with 50 ml of a saturated EDTA solution (pH=7, adjusted with NaOH) and twice with 50 ml of water. After drying the organic phase over sodium sulfate, contraction is carried out in vacuo to a solid residue.

Process 3

1 mmol of macrodiolide of the elaiophyline type is stirred in 100 ml of isopropanol at room temperature for 24 hours with 250 mg of NaBH$_4$. The excess of reductant is decomposed by addition of acetone. The solvent is removed by distillation in vacuo and the residue is taken up in ethyl acetate. After extracting by shaking with water, the organic phase is dried over sodium sulfate and removed by distillation in vacuo. Chromatography on 100 g of silica gel, having a linear gradient of ethyl acetate:hexane/1:5 in ethyl acetate (with compounds having $R_1=R_1'$ and $R_2, R_3 \neq H$) or chloroform:methanol/40:1 in chloroform/methanol/1:1 (with compounds having $R_1=R_1'$ and $R_2, R_3=H$) yields the reduced compounds.

Process 4

1 mmol of the compound from Example 22 (see Table 1) is suspended in 20 ml of methylene chloride and stirred for 20 hours at 25° C. under nitrogen with 6 mmol of SEM chloride or MEM chloride and 2 ml (12 mmol) of diisopropylethylamine. After the addition of 5 ml of methanol, the solvent is removed by distillation in vacuo. The residue is taken up in methylene chloride and extracted by shaking with water. After drying over sodium sulfate, the solvent is stripped off in vacuo. Chromatography on silica gel (100 g) having a linear gradient of ethyl acetate:hexane/1:5 in ethyl acetate (about 5 liters) yields the corresponding compounds.

Process 5

1 mmol of macrodiolide of the elaiophyline type is dissolved in 10 ml of dichloromethane and 10 ml of pyridine. After addition of an excess of carboxylic acid anhydride and 1 mmol of 4-dimethylaminopyridine, the mixture is stirred at room temperature until the reaction is complete according to the thin layer chromatogram (about 2 to 6 hours). Excess anhydride is decomposed by the addition of 5 ml of methanol with ice cooling. The mixture is diluted with 50 ml of ethyl acetate, first extracted three times each time using 20 ml of saturated sodium hydrogen carbonate solution, then using just so much 0.1 N HCl solution that the aqueous phase does not exceed pH 5, and finally one more time using 20 ml of saturated sodium hydrogen carbonate solution. After drying the organic phase over sodium sulfate and concentrating in vacuo, the product is either isolated by crystallization or by chromatography on silica gel.

Process 6

1 mmol of macrodiolide of the elaiophyline type is stirred with an excess of the relevant aldehyde or ketone, which in turn can be used as the solvent, at room temperature, if appropriate diluting with a co-solvent such as dichloromethane, chloroform or tetrahydrofuran, in the presence of catalytic amounts of an anhydrous Lewis acid such as i $ZnCL_2ZnI_2$, $FeCL_3$, $CuCL_2$ or $CuSO_4$, until the reaction is complete according to the thin layer chromatogram. After diluting with 50 ml of ethyl acetate and washing three times each time with 20 ml each of a saturated sodium hydrogen carbonate solution, the product is isolated by column chromatography on silica gel.

Process 7

1 mmol of macrodiolide of the elaiophyline type is dissolved in a suitable solvent or solvent mixture and 10% by weight of hydrogenation catalyst, preferably 10% of palladium on animal charcoal, are added. A reliable solvent system consists of a mixture of isopropanol/ethyl acetate/water in the volume ratio 4/3/2. The hydrogenation takes place at room temperature with magnetic stirring or shaking in a closed hydrogenation apparatus while maintaining a slight excess hydrogen pressure of up to 0.2 bar. Under these conditions, the reaction is completed in the course of 0.5 to 2 hours with the absorption of 4 mmol of $H_2$. After filtering off the catalyst and concentrating, the product must still be purified in some cases by recrystallization or column chromatography.

Process 8

1 mmol of macrodiolide of the elaiophyline type is dissolved in 10 to 100 ml of anhydrous methanol and up to 40% by weight of dried hydrogenation catalyst, preferably 10% palladium on animal charcoal, are added. The hydrogenation and product isolation takes place exactly as described for process 7.

The compounds synthesized according to the previously described processes 1 to 8 are shown in the following tables. The substituents in the radical $R^{1'}$ are designated by $R^{2'}$, $R^{3'}$, $R^{4'}$, $R^{5'}$ and $R^{7'}$. In Table 1, the various substituents of the elaiophyline derivatives are given for the purpose of identifying the compounds. In Table 2, the particular preparation process, the individual process parameters, the type of reagent, the relative concentration of the reagent (with reference to the starting compound of the elaiophyline type), the yield and also selected, characteristic analytical data for the compounds obtained are given. An explanation of the expressions used in the tables can be found at the end.

TABLE 1

| Compound | Precursor | Hydr. | $R^1$ | $R^2$ | $R^3$ | $R^4$ | $R^5$ | $R^7$ | $R^{1'}$ | $R^{2'}$ | $R^{3'}$ | $R^{4'}$ | $R^{5'}$ | $R^{7'}$ |
|---|---|---|---|---|---|---|---|---|---|---|---|---|---|---|
| 1 | Ela | — | II | Ac | Ac | H | H | — | II | Ac | Ac | H | H | — |
| 2 | Ela | — | II | Ac | Ac | H | H | — | II | H | Ac | H | H | — |
| 3 | Ela | — | II | H | Ac | H | H | — | II | H | Ac | H | H | — |
| 4 | Ela | — | II | H | Ac | H | H | — | II | H | H | H | H | — |
| 5 | Ela | — | II | p-Br—Bz | p-Br—Bz | H | H | — | II | p-Br—Bz | p-Br—Bz | H | H | — |
| 6 | Ela | — | II | p-Br—Bz | p-Br—Bz | H | H | — | II | H | p-Br—Bz | H | H | — |
| 7 | Ela | — | II | H | p-Br—Bz | H | H | — | II | H | p-Br—Bz | H | H | — |
| 8 | Ela | — | II | H | p-Br—Bz | H | H | — | II | H | H | H | H | — |
| 9 | Ela | — | II | Val | Val | H | H | — | II | H | Val | H | H | — |
| 10 | 1 | — | II | Ac | Ac | H | $CH_3$ | — | II | Ac | Ac | H | $CH_3$ | — |
| 11 | 1 | — | II | Ac | Ac | H | $C_2H_5$ | — | II | Ac | Ac | H | $C_2H_5$ | — |
| 12 | 2 | — | II | Ac | Ac | H | $CH_3$ | — | II | H | Ac | H | $CH_3$ | — |
| 13 | Ela | — | II | $2\text{-}C_5H_3O_2$ | $2\text{-}C_5H_3O_2$ | H | H | — | II | $2\text{-}C_5H_3O_2$ | $2\text{-}C_5H_3O_2$ | H | H | — |
| 14 | 13 | — | II | $2\text{-}C_5H_3O_2$ | $2\text{-}C_5H_3O_2$ | H | $CH_3$ | — | II | $2\text{-}C_5H_3O_2$ | $2\text{-}C_5H_3O_2$ | H | $CH_3$ | — |
| 15 | Ela | — | II |  | | H | H | — | II |  | | H | H | — |

TABLE 1-continued

| Compound | Precursor | Hydr. | R¹ | R² | R³ | R⁴ | R⁵ | R⁷ | R¹' | R² | R³ | R⁴ | R⁵ | R⁷ |
|---|---|---|---|---|---|---|---|---|---|---|---|---|---|---|
| 16 | Ela | — | II | \C=O/ | | H | H | — | II | C(O)Im | C(O)Im | H | H | — |
| 17 | 1 | — | II | Ac | Ac | H | H | — | III | Ac | Acn | H | — | H |
| 18 | 1 | — | III | Ac | Ac | H | — | H | III | Ac | Ac | H | — | H |
| 19 | 9 | — | II | Val | Val | H | H | — | III | Val | Val | H | — | H |
| 20 | 9 | — | III | Val | Val | H | — | H | III | Val | Val | H | — | H |
| 21 | 17 | — | II | Ac | Ac | H | CH₃ | — | III | Ac | Ac | H | — | H |
| 22 | Ela | — | II | H | H | H | CH₃ | — | II | H | H | H | CH₃ | — |
| 23 | 22 | — | II | SEM | SEM | H | CH₃ | — | II | SEM | SEM | H | CH₃ | — |
| 24 | 22 | — | II | MEM | MEM | H | CH₃ | — | II | MEM | MEM | H | CH₃ | — |
| 25(¹) | Ela | — | II | Ac | Ac | Ac | Ac | — | II | Ac | Ac | Ac | Ac | — |
| 26 | Ela | — | II | Mes | Mes | H | H | — | II | Mes | Mes | H | H | — |
| 27 | Ela | — | II | \C(CH₃)₂/ | | H | H | — | II | \C(CH₃)₂/ | | H | H | — |
| 28 | 27 | — | II | \C(CH₃)₂/ | | H | CH₃ | — | II | \C(CH₃)₂/ | | H | CH₃ | — |
| 29 | Ela | — | II | Bz | Bz | H | H | — | II | Bz | Bz | H | H | — |
| 30 | 29 | — | II | Bz | Bz | H | CH₃ | — | II | Bz | Bz | H | CH₃ | — |
| 31 | Ela | + | II | H | H | H | H | — | II | H | H | H | H | — |
| 32 | 1 | + | II | Ac | Ac | H | H | — | II | Ac | Ac | H | H | — |
| 33 | 2 | + | II | Ac | Ac | H | H | — | II | H | Ac | H | H | — |
| 34 | 3 | + | II | H | Ac | H | H | — | II | H | Ac | H | H | — |
| 35 | 4 | + | II | H | Ac | H | H | — | II | H | H | H | H | — |
| 36 | 5 | + | II | p-Br—Bz | p-Br—Bz | H | H | — | II | p-Br—Bz | p-Br—Bz | H | H | — |
| 37 | 6 | + | II | p-Br—Bz | p-Br—Bz | H | H | — | II | H | p-Br—Bz | H | H | — |
| 38 | 7 | + | II | H | p-Br—Bz | H | H | — | II | H | p-Br—Bz | H | H | — |
| 39 | 8 | + | II | H | p-Br—Bz | H | H | — | II | H | H | H | H | — |
| 40 | 31 | + | II | Val | Val | H | H | — | II | Val | Val | H | H | — |
| 41 | 53 | + | II | Ac | Ac | H | CH₃ | — | II | Ac | Ac | H | CH₃ | — |
| 42 | 32 | + | II | Ac | Ac | H | C₂H₅ | — | II | Ac | Ac | H | C₂H₅ | — |
| 43 | 33 | + | II | Ac | Ac | H | CH₃ | — | II | H | Ac | H | CH₃ | — |
| 44 | 31 | + | II | 2-C₅H₃OS | 2-C₅H₃OS | H | H | — | II | 2-C₅H₃OS | 2-C₅H₃OS | H | H | — |
| 45 | 44 | + | II | 2-C₅H₃OS | 2-C₅H₃OS | H | CH₃ | — | II | 2-C₅H₃OS | 2-C₅H₃OS | H | CH₃ | — |
| 46 | 31 | + | II | \C=O/ | | H | H | — | II | \C=O/ | | H | H | — |
| 47 | 31 | + | II | \C=O/ | | H | H | — | II | C(O)Im | C(O)Im | H | H | — |
| 48 | 32 | + | II | Ac | Ac | H | H | — | III | Ac | Ac | H | — | H |
| 49 | 32 | + | III | Ac | Ac | H | — | H | III | Ac | Ac | H | — | H |
| 50 | 40 | + | II | Val | Val | H | H | — | III | Val | Val | H | — | H |
| 51 | 40 | + | III | Val | Val | H | — | H | III | Val | Val | H | — | H |
| 52 | 48 | + | II | Ac | Ac | H | CH₃ | — | III | Ac | Ac | H | — | H |
| 53 | Ela | + | II | H | H | H | CH₃ | — | II | H | H | H | CH₃ | — |
| 54 | 31 | + | II | SEM | SEM | H | H | — | II | SEM | SEM | H | H | — |
| 55 | 31 | + | II | MEM | MEM | H | H | — | II | MEM | MEM | H | H | — |
| 56 | 25 | + | II | Ac | Ac | Ac | Ac | — | II | Ac | Ac | Ac | Ac | — |
| 57 | 31 | + | II | Bz | Bz | H | H | — | II | Bz | Bz | H | H | — |
| 58 | 57 | + | II | Bz | Bz | H | CH₃ | — | II | Bz | Bz | H | CH₃ | — |

TABLE 2

| Compound | Process | Reaction time (h) | Reaction temp. (°) | Reagent | Equivalents of reagent | Yield (%) |
|---|---|---|---|---|---|---|
| 1 | 1 | 24 | 20 | Ac₂O | 10 | 97 |
| 2 | 1 | 12 | −20 | Ac₂O | 5 | 62 |
| 3 | 1 | 14 | −20 | Ac₂O | 2.5 | 66 |
| 4 | 1 | 8 | −20 | Ac₂O | 1.5 | 46 |
| 5 | 1 | 10 | 20 | p-BrBzCl | 5 | 64 |

TABLE 2-continued

| | | | | | | |
|---|---|---|---|---|---|---|
| 6 | 1 | 3 | 20 | p-BrBzCl | 3.3 | 33 |
| 7 | 1 | 3 | −5 | p-BrBzCl | 2.6 | 54 |
| 8 | 1 | 5 | −35 | p-BrBzCl | 1.5 | 32 |
| 9 | 1 | 90 | 20 | Val$_2$O | 8 | 74 |
| 10 | 2 | 0.5 | 20 | CH$_3$OH | Solv. | 82 |
| 11 | 2 | 1 | 20 | C$_2$H$_5$OH | Solv. | 79 |
| 12 | 2 | 0.5 | 20 | CH$_3$OH | Solv. | 81 |
| 13 | 5 | 6 | 20 | (2-C$_5$H$_3$O$_2$)$_2$O | 12 | 83 |
| 14 | 2 | 0.5 | 20 | CH$_3$OH | Solv. | 90 |
| 15 | 1 | 72 | 20 | Im$_2$CO | 5 | 37 |
| 16 | 1 | 72 | 20 | Im$_2$CO | 5 | 35 |
| 17 | 3 | 12 | 20 | NaBH$_4$ | 6.5 | 33 |
| 18 | 3 | 12 | 20 | NaBH$_4$ | 6.5 | 42 |
| 19 | 3 | 12 | 20 | NaBH$_4$ | 6.5 | 30 |
| 20 | 3 | 12 | 20 | NaBH$_4$ | 6.5 | 50 |
| 21 | 2 | 0.5 | 20 | CH$_3$OH | Solv. | 80 |
| 22 | 2 | 0.5 | 20 | CH$_3$OH | Solv. | 95 |
| 23 | 4 | 24 | 20 | SEMCl | 8 | 35 |
| 24 | 4 | 24 | 20 | MEMCl | 8 | 30 |
| 25[t] | 5 | 12 | 20 | Ac$_2$O | 40 | 70 |
| 26 | 1 | 1 | 20 | MesCl | 5 | 41 |
| 27 | 6 | 14 | 30 | AcCH$_3$ | 100 | 20 |
| 28 | 2 | 0.5 | 20 | CH$_3$OH | Solv. | 90 |
| 29 | 5 | 6 | 20 | Bz$_2$O | 12 | 86 |
| 30 | 2 | 0.5 | 20 | CH$_3$OH | Solv. | 79 |
| 31 | 7 | 2 | 20 | H$_2$/Pd | 4 | 89 |
| 32 | 7 | 1.5 | 20 | H$_2$/Pd | 4 | 90 |
| 33 | 7 | 1.5 | 20 | H$_2$/Pd | 4 | 75 |
| 34 | 7 | 2 | 20 | H$_2$/Pd | 4 | 70 |
| 35 | 7 | 2 | 20 | H$_2$/Pd | 4 | 86 |
| 36 | 7 | 3 | 20 | H$_2$/Pd | 4 | 71 |
| 37 | 7 | 2.5 | 20 | H$_2$/Pd | 4 | 79 |
| 38 | 7 | 3 | 20 | H$_2$/Pd | 4 | 86 |
| 39 | 7 | 3 | 20 | H$_2$/Pd | 4 | 80 |
| 40 | 1 | 72 | 20 | Val$_2$O | 8 | 77 |
| 41 | 1 | 18 | 20 | Ac$_2$O | 20 | 82 |
| 42 | 2 | 1 | 20 | C$_2$H$_5$OH | Solv. | 89 |
| 43 | 2 | 0.5 | 20 | CH$_3$OH | Solv. | 84 |
| 44 | 5 | 8 | 20 | (2-C$_5$H$_3$OS)$_2$O | 12 | 79 |
| 45 | 2 | 0.5 | 20 | CH$_3$OH | Solv. | 90 |
| 46 | 1 | 72 | 20 | Im$_2$CO | 5 | 39 |
| 47 | 1 | 72 | 20 | Im$_2$CO | 5 | 31 |
| 48 | 3 | 12 | 20 | NaBH$_4$ | 6.5 | 28 |
| 49 | 3 | 12 | 20 | NaBH$_4$ | 6.5 | 44 |
| 50 | 3 | 12 | 20 | NaBH$_4$ | 6.5 | 39 |
| 51 | 3 | 12 | 20 | NaBH$_4$ | 6.5 | 54 |
| 52 | 2 | 0.5 | 20 | CH$_3$OH | Solv. | 85 |
| 53 | 8 | 22 | 20 | H$_2$/Pd | 4 | 87 |
| 54 | 4 | 24 | 20 | SEMCl | 8 | 32 |
| 55 | 4 | 24 | 20 | MEMCl | 8 | 38 |
| 56[t] | 8 | 2 | 20 | H$_2$/Pd | 4 | 77 |
| 57 | 5 | 6 | 20 | Bz$_2$O | 20 | 73 |
| 58 | 2 | 0.5 | 20 | CH$_3$OH | Solv. | 83 |

| | Selected analytical data[tt] | | | | | | |
|---|---|---|---|---|---|---|---|
| | | 20 | | | Elemental analysis | | |
| Compound | M.p. (°C.) | [α$_D$] (C = 1, CH$_3$OH) | FAB-MS MNa$^+$ | C (calc.) | C (found) | H (calc.) | H (found) |
| 1 | 186 | | 1215 | | | | |
| 2 | | | 1173 | | | | |
| 3 | | | 1131 | | | | |
| 4 | | | 1089 | | | | |
| 5 | 194 | | | | | | |
| 6 | 182 | | | | | | |
| 7 | 205 | | | | | | |
| 8 | 160 | | | | | | |
| 9 | 173 | | | | | | |
| 10 | | | 1243 | | | | |
| 11 | | | 1271 | | | | |
| 12 | | | 1201 | | | | |
| 13 | | | 1423 | | | | |
| 14 | | | 1451 | | | | |
| 15 | 207 | +3° | | | | | |
| 16 | 160 | −42° | | | | | |
| 17 | | | 1217 | | | | |
| 18 | | | 1219 | | | | |
| 19 | | | 1385 | | | | |
| 20 | | | 1387 | | | | |
| 21 | | | 1231 | | | | |
| 22 | | | 1075 | | | | |
| 23 | | | 1595 | | | | |
| 24 | | | 1427 | | | | |

TABLE 2-continued

| | | | | | | |
|---|---|---|---|---|---|---|
| 25[(i)] | | +10° | 61.75 | 61.55 | 7.69 | 7.65 |
| 26 | | | 1359 | | | |
| 27 | | | 1127 | | | |
| 28 | | | 1155 | | | |
| 29 | | −96° | | | | |
| 30 | | | 68.64 | 68.72 | 7.40 | 7.60 |
| 31 | 198 | −77° | | | | |
| 32 | 125 | −86° | | | | |
| 33 | | | 1181 | | | |
| 34 | | | 1139 | | | |
| 35 | | | 1097 | | | |
| 36 | | | 55.79 | 56.95 | 6.16 | 6.27 |
| 37 | | | 56.93 | 56.72 | 6.69 | 6.89 |
| 38 | | | 58.37 | 58.12 | 7.35 | 7.50 |
| 39 | | | 60.23 | 60.04 | 8.20 | 8.44 |
| 40 | | | 1391 | | | |
| 41 | | −53° | | | | |
| 42 | | | 1279 | | | |
| 43 | | | 1209 | | | |
| 44 | | | 60.30 | 59.99 | 7.11 | 6.89 |
| 45 | | | 60.77 | 60.57 | 7.25 | 7.39 |
| 46 | | | 61.97 | 62.20 | 8.54 | 8.33 |
| 47 | | | 60.65 | 61.00 | 7.92 | 7.69 |
| 48 | | | 1225 | | | |
| 49 | | | 1227 | | | |
| 50 | | | 1393 | | | |
| 51 | | | 1395 | | | |
| 52 | | | 1239 | | | |
| 53 | 114 | −49.5 | | | | |
| 54 | | | 1603 | | | |
| 55 | | | 1435 | | | |
| 56[(i)] | | | 61.38 | 61.30 | 8.24 | 8.30 |
| 57 | 190 | −106 | | | | |
| 58 | | | 68.27 | 67.97 | 7.91 | 7.99 |

The compounds in general melt with decomposition. All remaining substances are amorphous solids. The structure assignment is based in particular on $^1$H, $^{13}$C, 2D-DNMR, FAB-MS and IR spectroscopy.

| Key to the table | |
|---|---|
| Ela: | elaiophyline $R^1, R^{1'}$ = II and $R^2, R^3, R^4, R^5$ = H |
| Ac: | —CO—CH$_3$ |
| p-Br—Bz: | para-bromobenzoyl |
| Val: | —Co—(CH$_2$)$_3$CH$_3$ |
| Solv.: | reagent = solvent |
| 2-C$_5$H$_3$O$_2$: | 2-furoyl |
| Im$_2$CO: | carbonyldiimidazole |
| Im: | 1-imidazolyl |
| SEM: | (CH$_3$)$_3$SiCH$_2$CH$_2$OCH$_2$— |
| MEM: | CH$_3$OCH$_2$CH$_2$OCH$_2$— |
| Mes: | —SO$_2$CH$_3$ |
| Bz: | benzoyl |
| 2-C$_5$H$_3$OS: | 2-thienoyl |
| Hydr.: | in this column is given whether the macrodiolide ring is hydrogenated (+) or not (−) |
| II or III: | in the columns under $R^1$ and $R^{1'}$ is given which formula type (see formula I) the substituents $R^1$ and $R^{1'}$ belong to. |

Anthelmintic action of the elaiophyline derivatives

The anthelmintic action of the elaiophyline derivatives was investigated in lambs having a body weight of 30 to 40 kg. for this, the lambs were artificially infected with infective stages of abomasum nematodes (Haemunchus cortortus). After the end of the development time (prepatency period) of the nematodes, the administration of the elaiophyline derivatives took place.

By coproscopic investigations before and up to 14 days after the administration of the elaiophyline derivatives and subsequent section with helminthological working up, the percentage reduction of the sheep nematodes was ascertained (see Table 3). Elaiophyline was used as the comparison substance. Additionally, the antibacterial activity of the elaiophyline derivatives according to the invention against Staph. aureus and Strept. pyogenes was also ascertained. Surprisingly, the compounds according to the invention show no or only very low antibacterial activity. Precisely for this reason, the compounds according to the invention are in particular suitable for use as anthelmintics, since here an antibacterial action is undesired.

TABLE 3

| Administered compound from Example | Dose (mg/kg) | Reduction of H. contortus (%) | Antibacterial activity (μg/ml) against | |
|---|---|---|---|---|
| | | | Staph. aureus | Strept. pyogenes |
| Elaiophyline | 2.5 (s.c.) | 35–45 | 1.56 | 1.56 |
| | 5.0 (oral) | 70–95 | | |
| 1 | 2.5 (s.c.) | 70–90 | >100 | >100 |
| | 5.0 (oral) | 40–60 | | |
| 2 | 2.5 (s.c.) | 50–70 | >100 | 6.25 |
| | 5.0 (oral) | 30–40 | | |
| 5 | 2.5 (s.c.) | 5–10 | >100 | >100 |
| | 5.0 (oral) | 5–10 | | |
| 8 | 2.5 (s.c.) | 50–70 | >100 | 3.13 |
| | 5.0 (oral) | 10–20 | | |
| 9 | 2.5 (s.c.) | 50–70 | 50.0 | 50.0 |
| | 5.0 (oral) | 50–70 | | |

TABLE 3-continued

| Administered compound from Example | Dose (mg/kg) | Reduction of H. contortus (%) | Antibacterial activity (μg/ml) against | |
|---|---|---|---|---|
| | | | Staph. aureus | Strept. pyogenes |
| 10 | 2.5 (s.c.) | 10–20 | >100 | >100 |
| | 5.0 (oral) | 30–50 | | |
| 15 | 2.5 (s.c.) | 5–10 | >100 | >100 |
| | 5.0 (oral) | 5–10 | | |
| 16 | 2.5 (s.c.) | 5–10 | >100 | >100 |
| | 5.0 (oral) | — | | |
| 17 | 2.5 (s.c.) | 30–50 | 25.0 | 25.0 |
| | 5.0 (oral) | 30–50 | | |
| 22 | 2.5 (s.c.) | 30–40 | 3.13 | 1.56 |
| | 5.0 (oral) | 60–75 | | |
| 29 | 2.5 (s.c.) | 10–20 | >100 | >100 |
| | 5.0 (oral) | 60–80 | | |
| 31 | 2.5 (s.c.) | 30–40 | >100 | >100 |
| | 5.0 (oral) | 50–75 | | |
| 32 | 2.5 (s.c.) | 50–60 | >100 | >100 |
| | 5.0 (oral) | 40–60 | | |
| 41 | 2.5 (s.c.) | 40–60 | >100 | >100 |
| | 2.5 (oral) | 60–80 | | |
| 53 | 2.5 (s.c.) | 40–50 | 25 | 6.25 |
| | 3.8 (oral) | 60–75 | | |
| 57 | 2.5 (s.c.) | 20–30 | >100 | >100 |
| | 5.0 (oral) | 40–60 | | |

We claim:
1. An elaiophyline derivative of the formula I

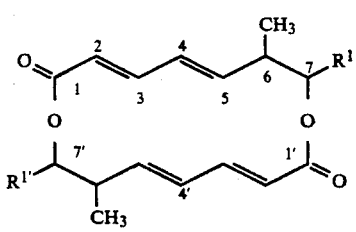

where the C-13 C double bonds in the macrodielide ring of the compound of the formula I can also be hydrogenated and in which
$R^1$ is a radical of the formula II or III

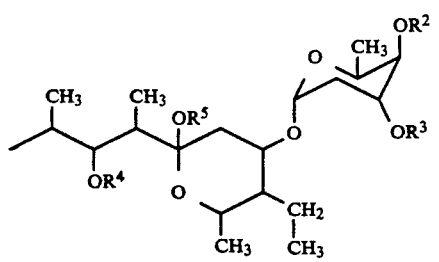

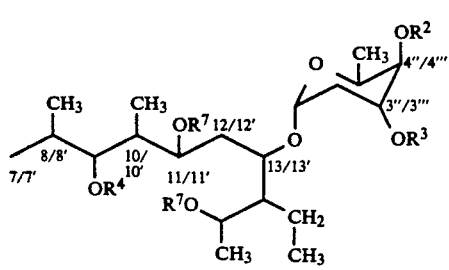

in which
$R^2$ and $r^3$ are identical or different and denote hydrogen or a radical of the formula IV or IV'

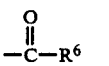 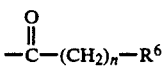

in which
n denotes 1 to 3 and
$R^6$ denotes $C_1$–$C_{15}$-alkyl, $C_2$–$C_{15}$-alkenyl, $C_2$–$C_{15}$-alkynyl, $C_3$–$C_9$-cycloalkyl, a radical selected from the group consisting of phenyl, naphthyl, thiophene, furan, pyridine, pyrimidine and pyrazine, where said radical can be substituted by halogen, nitro, cyano, hydroxyl, $C_1$–$C_4$-alkyl or $C_1$–$C_4$-alkoxy and where for the case in which $R^3$ is hydrogen, $R^2$ is also hydrogen, or in which
$R^2$ and $R^3$ are identical and denote $C_1$–$C_4$-alkyl, benzyl, allyl, methoxyethoxymethyl, methoxymethyl, β-trimethylsilylethoxymethyl, trimethylsilyl, triethylsilyl, dimethylphenylsilyl, dimethylcyclohexylsilyl or dimethyl tertiary butylsilyl or
$R^2$ and $R^3$ denote sulfonates of the formula $SO_2R$
in which
$R^{10}$ denotes $C_1$–$C_{10}$-aklyl, phenyl or p-tolyl or
$R^2$ and $R^3$ represent a radical of the formula V or V'

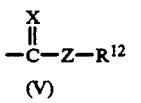 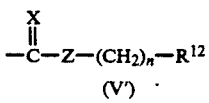

in which
n denotes 1 to 3
X denotes oxygen or sulfur
$R^{12}$ denotes $C_1$–$C_{15}$-alkyl, $C_3$–$C_9$-cycloalkyl, phenyl, naphthyl, pyridyl, pyrimidyl or pyrazinyl, where the phenyl, napthyl, pyridyl, pyrimidyl or pyrazinyl radicals can be substituted by halogen, nitro, cyano or $C_1$–$C_4$-alkoxy and Z denotes oxygen, —N—H or a radical —N—R$^{12}$ or —N—(CH$_2$)$_n$— R$^{12}$, where n and R$^{12}$ have the above-mentioned meanings or in which R$^2$ and R$^3$ together represent a radical of the formula VI

(VI)

in which

R$^8$ and R$^9$ are identical or different and denote hydrogen or unbranched C$_1$-C$_{10}$-alkyl or where R$^8$ and R$^9$ represent an alkylene chain, which together with the carbon atom carrying it, forms a 5-, 6- or 7-membered ring or in which R$^2$ and R$^3$, for the case in which R$^1$ is a radical of the formula II, are identical and represent a radical of the formula VIII

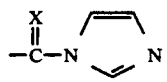
(VIII)

in which

X denotes oxygen or sulfur or

R$^2$ and R$^3$, for the case in which R$^1$ is a radical of the formula

II, together represent a radical of the formula

wherein

X denotes oxygen or sulfur and in which

R$^4$, provided that R$^2$ and R$^3$ are hydrogen, denotes hydrogen or, for the case in which R$^2$ and R$^3$ do not denote hydrogen, is hydrogen or a radical of the formula IV or IV'

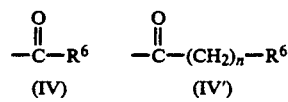

n and R$^6$ have the above-mentioned meanings and

R$^5$ is hydrogen or a radical of the formula —(CH$_2$)$_n$—R$^6$ where n and R$^6$ have the above-mentioned meanings and in which R$^7$ denotes hydrogen or—provided that R$^2$, R$^3$ and R$^4$ do not simultaneously denote hydrogen—forms a radical of the formula IV or IV'—as defined above— and in which

R$^{1'}$ has the same meaning as R$^1$, where the two radicals R$^1$ and R$^{1'}$ can be substituted both by identical—except for the radicals R$^4$ and R$^5$ and for the case in which R$^2$ and R$^3$ together form a radical of the formula VI—and different substituents, with the exception that when R$^1$ is a radical of the formula II in which R$^2$ and R$^3$ form a radical of the formula VIII or in which R$^2$ and R$^3$ together form a radical of the formula >C=X, for R$^{1'}$ the radicals R$^2$ and R$^3$ in the radical of the formula II or III are not simultaneously hydrogen, excluding elaiophyline itself, elaiophyline having a hydrogenated macrodiolide ring, and also compounds of the formula I, wherein the macrodiolide ring is hydrogenated or unhydrogenated and in which R$^1$ and R$^{1'}$ are identical or different and represent a radical of the formula II or III, wherein R$^2$ and R$^3$ denote hydrogen or acetyl and R$^4$ and R$^5$ or R$^7$ denote hydrogen and likewise also excluding the compounds of the formula I in which the macrodiolide ring is unhydrogenated and wherein R$^1$ and R$^{1'}$ simultaneously represent a radical of the formula II, wherein R$^2$, R$^3$ and R$^4$ denote hydrogen and wherein R$^5$ denotes a radical of the formula —(CH$_2$)$_n$—R$^6$ where n and R$^6$ have the above-mentioned meanings.

2. The elaiophyline derivative of the formula I as claimed in claim 1, where the C—C double bonds in the macrodiolide ring of the compound of the formula I can also be hydrogenated and in which R$^1$ is a radical of the formula II or III, as given in claim 1, in which R$^2$ and R$^3$ are identical or different and denote hydrogen or a radical of the formula IV or IV, as given in claim 1, in which n denotes 1 to 3 and R$^6$ denotes C$_1$-C$_5$-alkyl, C$_2$-C$_5$-alkenyl, C$_2$-C$_6$-alkynyl, C$_3$-C$_6$-cycloalkyl, phenyl or furyl or thienyl, where the phenyl, furyl and thienyl radicals can be substituted by halogen, nitro, cyano, hydroxyl, C$_1$-C$_4$-alkyl or C$_1$-C$_4$-alkoxy and where, for the case in which R$^3$ is hydrogen, R$^2$ is also hydrogen, or in which R$^2$ and R$^3$ are identical and denote methoxyethoxymethyl, methoxymethyl, β-trimethylsilylethoxymethyl, trimethylsilyl, triethylsilyl, dimethylphenylsilyl, dimethycyclohexylsilyl or dimethyl tertriary butylsilyl or R$^2$ and R$^3$ denote sulfonates of the formula SO$_2$R$^{10}$, in which R$^{10}$ denotes C$_1$-RC$_4$-alkyl, phenyl or p-tolyl or R$^2$ and R$^3$ represent a radical of the formula V or V', as given in claim 1, in which n denotes 1, X denotes oxygen, R$^{12}$ denotes C$_1$-C$_4$-alkyl, C$_3$-C$_6$-cycloalkyl, phenyl or naphthyl, where the phenyl or napthyl radical can be substituted by halogen, nitro, cyano or C$_1$-C$_4$-alkoxy and Z denotes oxygen or —N—H or in which R$^2$ and R$^3$ together represent a radical of the formula VI as given in claim 1, in which R$^8$ and R$^9$ are identical or different and denote hydrogen or unbranched C$_1$-C$_4$-alkyl or where $R^8$ and $R^9$ represent an alkylene chain which, together with carbon atom carrying it forms a 5- or 6-membered ring or in which $R^2$ and $R^3$, for the case in which $R^1$ is a radical of the formula II, as given in claim 1, are identical and represent a radical of the formula VIII, as given in claim 1, in which X denotes oxygen or $R^2$ and $R^3$, for the case in which $R^1$ is a radical of the formula II, as given in claim 1, together represent a radical of the formula $>C=X$, in which X denotes oxygen and in which $R^4$, provided $R^2$ and $R^3$ are hydrogen, denotes hydrogen or, for the case in which $R^2$ and $R^3$ do not denote hydrogen, is hydrogen or a radical of the formula IV or IV', as given in claim 1, in which n is 1 to 3 and $R^6$ has the above-mentioned meanings, and $R^5$ is hydrogen or a radial of the formula $-(CH_2)_N-R^6$ where n is 1 to 3 and $R^6$ has the meanings as given above, and in which $R^7$ denotes hydrogen or —provided $R^2$, $R^3$ and $R^4$ do not simultaneously denote hydrogen—forms a radical of the formula IV or IV' as given in claim 1 and defined above and in which $R^{1'}$ has the same meaning as $R^1$, in which the two radicals $R^1$ and $R^{1'}$ can be substituted both by identical substituents and also—except for the radicals $R^4$ and $R^5$ and for the case in which $R^2$ and $R^3$ together form a radical of the formula VI—different substituents, with the exception that when $R^1$ is a radical of the formula II as given in claim 1 in which $R^2$ and $R^3$ form a radical of the formula VIII as given in the claim 1, or in which $R^2$ and $R^3$ together form a radical of the formula $>C=X$, for $R^{1'}$ the radicals $R^2$ and $R^3$ in the radical of the formula II or III as given in claim 1, are not simultaneously hydrogen, excluding elaiophyline itself, elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II or III, in which $R^2$ and $R^3$ denote hydrogen or acetyl and $R^4$ and $R^5$ or $R^7$ denote hydrogen and likewise also excluding the compounds of the formula I, in which the macrodiolide ring is unhydrogenated and in which $R^1$ and $R^{1'}$ simultaneously represent a radical of the formula II, in which $R^2$, $R^3$ and $R^4$ denote hydrogen and in which $R^5$ denotes a radical of the formula $-(CH_2)_n-R^6$ where n and $R^6$ have the above-mentioned meanings.

3. An elaiophyline derivative of the formula I as claimed in claim 1, where the C—C double bonds in the macrodiolide ring of the compound of the formula I can also be hydrogenated and in which $R^1$ is a radical of the formula II or III—as given in claim 1, in which $R^2$ and $R^3$ are identical or different and denote hydrogen or a radical of the formula IV or IV', as given in claim 1 in which n denotes 1, $R^6$ denotes $C_1-C_5$-alkyl, cyclohexyl, phenyl, furyl or thienyl, in which the phenyl furyl, and thienyl radicals can be substituted with fluorine, chlorine or bromine and where, for the case in which $R^3$ is hydrogen, $R^2$ is also hydrogen, or in which $R^2$ and $R^3$ are identical and denote methoxyethoxymethyl, methoxymethyl, $\beta$-trimethylsilylethoxymethyl, trimethylsilyl, triethylsilyl, dimethylphenylsilyl, dimethycyclohexylsilyl or dimethyl tertiary butylsilyl or $R^2$ and $R^3$ denote sulfonates of the formula $SO_2R^{10}$ in which $R^{10}$ denotes methyl, phenyl or p-tolyl or $R^2$ and $R^3$ represent a radical of the formula V or V', as given in claim 1, in which n denotes 1 x denotes oxygen $R^{12}$ denotes cyclohexyl, or phenyl or napthyl, where the phenyl or napthyl radical is optionally substituted by halogen, nitro, cyano or $C_1-C_4$-alkoxy and Z denotes oxygen or —N—H, or in which $R^2$ and $R^3$ together represent a radical of the formula VI, as given in claim 1, in which $R^8$ and $R^9$ are identical or different and denote hydrogen or unbranched $C_1-C_4$-alkyl or where $R^8$ and $R^9$ represent an alkylene chain which, together with the carbon atom carrying it forms a 5- or 6-membered ring or in which $R^2$ and $R^3$, for the case in which $R^1$ is a radical of the formula II, as given in claim 1, are identical and represent a radical of the formula VIII, as given in claim 1, in which X denotes oxygen or $R^2$ and $R^3$, for the case in which $R^1$ is a radical of the formula II, as given in claim 1, together represent a radical of the formula $C=X$, in which X denotes oxygen and in which $R^4$, provided $R^2$ and $R^3$ are hydrogen, denotes hydrogen or, for the case in which $R^2$ and $R^3$ do not denote hydrogen, is hydrogen or a radical of the formula IV or IV', as given in claim 1, in which n is 1 and $R^6$ has the meanings given above and $R^5$ is hydrogen or a radical of the formula $-(Ch_2)_n-R^6$ in which n is 1 and $R^6$ has the meanings given above and in which $R^7$ denotes hydrogen or—provided $R^2$, $R^3$ and $R^4$ do not simultaneously denote hydrogen—forms a radical of the formula IV or IV'—as given in claim 1 and defined above — and in which $R^{1'}$ has the same meaning as $R^1$, where the two radicals $R^1$ and $R^{1'}$ can be substituted both with identical substituents and also —except for the radicals $R^4$ and $R^5$ and for the case in which $R^2$ and $R^3$ together form a radical of the formula VI—different substituents, with the exception that when $R^1$ is a radical of the formula II, as given in claim 1, in which $R^2$ and $R^3$ form a radical of the formula VIII, as given in claim 1, or in which $R^2$ and $R^3$ together form a radical of the formula

for $R^{1'}$ the radicals $R^2$ and $R^3$ in the radial of the formula II or III, as given in claim 1, are note simultaneously hydrogen,
excluding elaiophyline itself, elaiophyline having a hydrogenated macrodiolide ring, and also compounds of the formula I, in which the macrodiolide ring is hydrogenated or unhydrogenated and in which $R^1$ and $R^{1'}$ are identical or different and represent a radical of the formula II or III, in which $R^2$ and $R^3$ denote hydrogen or acetyl and $R^4$ and $R^5$ or $R^7$ denote hydrogen and likewise also excluding the compounds of the formula I in which the macrodiolide ring is not hydrogenated and in which $R^1$ and $R^{1'}$, simultaneously represent a radical of the formula II, in which $R^2$, $R^3$ and $R^4$ denote hydrogen and in which $R^5$ denotes a radical of the formula $-(CH_2)_n-R^6$ where n and $R^6$ have the above-mentioned meanings.

4. A pharmaceutical composition for use in the treatment of anthelmintic disorders comprising a therapeutically effective amount of at least one of the elaiophyline derivatives of the formula I as claimed in claim 1, wherein the C—C double bonds in the macrodiolide ring of the compound of the formula (I) can also be hydrogenated and in which $R^1$ is a radical of the formula II or III, in which $R^2$ and $R^3$ are identical or different and denote hydrogen, or a radical of the formula IV or IV' in which
n denotes 1 to 3 and
$R^6$ denotes $C_1-C_{15}$-alkenyl, $C_2-C_{15}$-alkynyl, $C_3-C_9$-cycloalkyl, aryl or heteroaryl radical selected from the group consisting of phenyl, naphthyl, thiophene, furan, pyridine, pyrimidine or pyrazine, wherein said aryl and heteroaryl radicals can be substituted by halogen, nitro, cyano, hydroxyl, $C_1-C_4$-alkyl or $C_1-C_4$-alkoxy and where for the case in
which $R^3$ is hydrogen, $R^2$ is also hydrogen,
or in which
$R^2$ and $R^3$ are identical and denote $C_1-C_4$-alkyl, benzyl, allyl, methoxyethoxymethyl, methoxymethyl, $\beta$-trimethylsilylethoxymethyl, trimethylsilyl, triethylsilyl, dimethylphenylsilyl, dimethylcyclohexylsilyl or dimethyl tertiary butylsilyl
or
$R^2$ and $R^3$ denote sulfonates of the formula $SO_2R^{10}$
in which
$R^{10}$ denotes $C_1-C_{10}$-alkyl, phenyl or p-tolyl
or
$R^2$ and $R^3$ represent a radical of the formula V or V'
in which
n denotes 1 to 3
X denotes oxygen or sulfur
$R^{12}$ denotes $C_1-C_{15}$-alkyl, $C_3-C_9$-cycloalkyl, phenyl, napthyl, pyridyl, pyrimidyl or pyrazinyl, where the phenyl, napthyl, pyridyl, pyrimidyl or pyrazinyl radicals can be substituted by halogen, nitro, cyano or $C_1-C_4$-alkoxy and
denotes oxygen, —N—H or a radical $-N-R^{12}$ or $-N-(CH_2)-$
$R^{12}$, where n and $R^{12}$ have the above-mentioned meanings
or in which
$R^2$ and $R^3$ together represent a radical of the formula VI
in which
$R^8$ and $R^9$ are identical or different and denote hydrogen or unbranched $C_1-C_{10}$-alkyl or where
$R^8$ and $R^9$ represent an alkylene chain, which together with the carbon atom carrying it, forms a 5-, 6- or 7-membered ring
or in which
$R^2$ and $R^3$, for the case in which $R^1$ is a radical of the formula II, are identical and represent a radical of the formula VIII
in which
X denotes oxygen or sulfur
or
$R^2$ and $R^3$, for the case in which $R^1$ is a radical of the formula II, together represent a radical of the formula

wherein
X denotes oxygen or sulfur
and in which
$R^4$, provided that $R^2$ and $R^3$ are hydrogen, denotes hydrogen or, for the case in which $R^2$ and $R^3$ do not denote hydrogen, is hydrogen or a radical of the formula IV or IV'
n and $R^6$ have the above-mentioned meanings
and
$R^5$ is hydrogen or a radical of the formula $-(CH_2)_n-R^6$
where
n and $R^6$ have the above-mentioned meanings
and in which
$R^7$ denotes hydrogen or—provided that $R^2$, $R^3$ and $R^4$ do not simultaneously denote hydrogen—forms a radical of the formula IV or IV' as defined above—
and in which
$R^{1'}$, has the same meaning as $R^1$, where the two radicals $R^1$ and $R^{1'}$ can be substituted both by identical-13 except for the radicals $R^4$ and $R^5$ and for the case in which $R^2$ and $R^3$ together form a radical of the formula VI—and different substituents, with the exception that when $R^1$ is a radical of the formula II in which $R^2$ and $R^3$ form a radical of the formula VIII or in which $R^2$ and $R^3$ together form a radical of the formula $>C=X$, for $R^{1'}$ the radicals $R^2$ and $R^3$ in the radical of the formula II or III are note simultaneously hydrogen,
excluding elaiophyline, together with an inert carrier.

5. A pharmaceutical composition for use in the treatment of anthelmintic disorders comprising a therapeutically effective amount of at least one of the elaiophyline derivatives of the formula I, as claimed in claim 2, wherein the C—C double bonds in the macrodiolide ring of the compound of the formula I can also be hydrogenated and in which $R^1$ is a radical of the formula II or III, in which $R^2$ and $R^3$ are identical or different and denote hydrogen or a radical of the formula IV or IV,
in which
n denotes 1 to 3 and
$R^6$ denotes $C_1$-$C_5$-alkyl, $C_2$-$C_5$-alkenyl, $C_2$-$C_6$-alkynyl, $C_3$-$C_6$ cycloalkyl, phenyl or furyl or thienyl, where the phenyl, furyl and thienyl radicals can be substituted by halogen, nitro, cyano, hydroxyl, $C_1$-$C_4$-alkyl or $C_1$-$C_4$-alkoxy and where, for the case in which $R^3$ is hydrogen, $R^2$ is also hydrogen,
or in which
$R^2$ and $R^3$ are identical and denote methoxyethoxymethyl, methoxymethyl, β-trimethylsily ethoxymethyl, trimethylsilyl, triethylsilyl, dimethylphenylsilyl, dimethycyclohexylsilyl or dimethyl tertiary butylsilyl
or
$R^2$ and $R^3$ denote sulfonates of the formula $SO_2R^{10}$,
in which
$R^{10}$ denotes $C_1$-$C_4$-alkyl, phenyl or p-tolyl
or
$R^2$ and $R^3$ represent a radical of the formula V or V',
in which
n denotes 1,
X denotes oxygen,
$R^{12}$ denotes $C_1$-$C_4$-alkyl, $C_3$-$C_6$-cycloalkyl or phenyl and naphthyl, where the phenyl and napthyl radical can be substituted by halogen, nitro, cyano or $C_2$-$C_4$-alkoxy and
Z denotes oxygen or —N—H
or in which
$R^2$ and $R^3$ together represent a radical of the formula VI, in which $R^8$ and $R^9$ are identical or different and denote hydrogen or unbranched $C_1$-$C_4$-alkyl
or where
$R^8$ and $R^9$ represent an alkylene chain which, together with carbon atom carrying it forms a 5- or 6-membered ring
or in which
$R^2$ and $R^3$, for the case in which $R^1$ is a radical of the formula II are identical and represent a radical of the formula VIII,
in which
X denotes oxygen
or
$R^2$ and $R^3$, for the case in which $R^1$ is a radical of the formula II together represent a radical of the formula

in which
X denotes oxygen
and in which
$R^4$, provided $R^2$ and $R^3$ are hydrogen, denotes hydrogen or, for the case in which $R^2$ and $R^3$ do not denote hydrogen, is hydrogen or a radical of the formula IV or IV',
in which
n is 1 to 3 and $R^6$ has the meanings as given above, and
$R^5$ is hydrogen or a radical of the formula —($CH_2$)$_n$—$R^6$
where n is 1 to 3 and $R^6$ has the meanings as given above,
and in which
$R^7$ denotes hydrogen or—provided $R^2$, $R^3$ and $R^4$ do not simultaneously denote hydrogen—forms a radical of the formula IV or IV' and defined above
and in which
$R^{1'}$ has the same meaning as $R^1$, in which the two radicals $R^1$ and $R^{1'}$ can be substituted both by identical substituents and also—except for the radicals $R^4$ and $R^5$ and for the case in which $R^2$ and $R^3$ together form a radical of the formula VI—different substituents, with the exception that when $R^1$ is a radical of the formula II in which $R^2$ and $R^3$ form a radical of the formula VIII, or in which $R^2$ and $R^3$ together form a radical of the formula C=X, for $R^{1'}$ the radicals $R^2$ and $R^3$ in the radical of the formula II or III, are note simultaneously hydrogen,
excluding elaiophyline, together with an inert carrier.

6. A pharmaceutical composition for use in the treatment of anthelmintic disorders comprising a therapeutically effective amount of at least one of the elaiophyline derivatives of the formula I, as claimed in claim 3,
wherein the C—C double bonds in the macrodiolide ring of the compound of the formula I can also be hydrogenated and in which $R^1$ is a radical of the formula II or III, in which
$R^2$ and $R^3$ are identical or different and denote hydrogen or a radical of the formula IV or IV', in which
n denotes 1,
$R^6$ denotes $C_1$-$C_5$-alkyl, cyclohexyl, phenyl, furyl or thienyl, in which the phenyl, furyl, and thienyl radicals are which can be substituted with fluorine, chlorine or bromine and where, for the case in which $R^3$ is hydrogen, $R^2$ is also hydrogen,
or in which
$R^2$ and $R^3$ are identical and denotes methoxyethoxymethyl, methoxymethyl, β-trimethylsilylethoxymethyl, trimethylsilyl, triethylsilyl, dimethylphenylsilyl, dimethycyclohexylsilyl or dimethyl tertiary butylsilyl
or
$R^2$ and $R^3$ denote sulfonates of the formula $SO_2R^{10}$
in which
$R^{10}$ denotes methyl, phenyl or p-tolyl
or
$R^2$ and $R^3$ represent a radical of the formula V or V',
in which
n denotes 1
x denotes oxygen
$R^{12}$ denotes cyclohexyl, or phenyl or napthyl, where the phenyl or napthyl radical can be substituted by halogen, nitro, cyano or $C_1$-$C_4$-alkoxy and
Z denotes oxygen or —N—H,
or in which
$R^2$ and $R^3$ together represent a radical of the formula VI,
in which
$R^8$ and $R^9$ are identical or different and denote hydrogen or unbranched $C_1$-$C_4$-alkyl or where
$R^8$ and $R^9$ represent an alkylene chain which, together with the carbon atom carrying it forms a 5- or 6-membered ring
or in which
$R^2$ and $R^3$, for the case in which $R^1$ is a radical of the formula II, are identical and represent a radical of the formula VIII,
in which X denotes oxygen
or
R² and R³ for the case in which R¹ is a radical of the formula II, together represent a radical of the formula C=X,
in which
X denotes oxygen
and in which
R⁴, provided R² and R³ are hydrogen, denotes hydrogen or, for the case in which R² and R³ do not denote hydrogen, is hydrogen or a radical of the formula IV or IV',
in which
n is 1 and R⁶ has the meanings given above
and
R⁵ is hydrogen or a radical of the formula —(CH₂.)ₙ—R⁶
in which
n is 1 and R⁶ has the meanings given above
and in which
R⁷ denotes hydrogen or—provided R², R³ and R⁴ do not simultaneously denote hydrogen—forms a radical of the formula IV or IV'—and defined above—
and in which
R¹' has the same meaning as R¹, where the two radicals R¹ and R¹' can be substituted both with identical substituents and also —except for the radicals R⁴ and R⁵ and for the case in which R² and R³ together form a radical of the formula VI—different substituents, with the exception that when R¹ is a radical of the formula II, in which R² and R³ form a radical of the formula VIII, or in which R² and R³ together form a radical of the formula

for R¹ the radicals R² and R³ in the radical of the formula II or III, are note simultaneously hydrogen,
excluding elaiophyline, together with an inert carrier.

7. A method for treating a patient suffering from an anthelmintic disease which comprises administering to said patient a therapeutic amount of a pharmaceutical composition as claimed in claim 4.

8. A method of treating a patient suffering from an anthelmintic disease which comprises administering to said patient a therapeutic amount of a pharmaceutical composition as claimed in claim 5.

9. A method of treating a patient suffering from an anthelmintic disease which comprises administering to said patient a therapeutic amount of a pharmaceutical composition as claimed in claim 6.

* * * * *

UNITED STATES PATENT AND TRADEMARK OFFICE
CERTIFICATE OF CORRECTION

PATENT NO. : 5,011,827

DATED : April 30, 1991

INVENTOR(S) : Gerhard Kretzschmar et al.

It is certified that error appears in the above-identified patent and that said Letters Patent is hereby corrected as shown below: Title page, item [57]:

Abstract, figure (III), change " 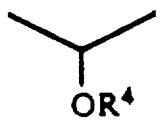 " to -- 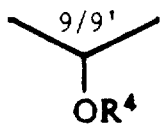 --.

Abstract, second to last line, change "lattere" to --latter--.

Claim 1, column 25, line 40, change "C-13 C" to --C-C--.

Claim 1, column 25, line 40, change "macrodielide" to --macrodiolide--.

Claim 1, column 25, line 60, change " 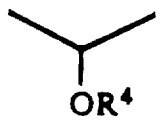 " to -- 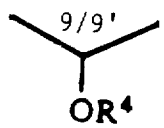 --.

UNITED STATES PATENT AND TRADEMARK OFFICE
CERTIFICATE OF CORRECTION

PATENT NO. : 5,011,827

DATED : April 30, 1991

INVENTOR(S) : Gerhard Kretzschmar et al.

It is certified that error appears in the above-identified patent and that said Letters Patent is hereby corrected as shown below:

Claim 1, column 25, line 67, change "$r^3$" to --$R^3$--.

Claim 1, column 26, line 49, change "$SO_2R$" to --$SO_2R^{10}$--.

Claim 1, column 26, line 51, change "aklyl to --alkyl--.

Claim 1, column 26, line 66, change "napthyl" to --naphthyl--.

Claim 2, column 28, line 31, after "or" change "IV" to --IV'--.

Claim 2, column 28, line 46, change "dimethycyclohexylsilyl" to --"dimethylcyclohexylsilyl--.

Claim 2, column 28, line 47, change "tertriary" to --tertiary--.

UNITED STATES PATENT AND TRADEMARK OFFICE
CERTIFICATE OF CORRECTION

PATENT NO. : 5,011,827

DATED : April 30, 1991

INVENTOR(S) : Gerhard Kretzschmar et al.

It is certified that error appears in the above-identified patent and that said Letters Patent is hereby corrected as shown below:

Claim 2, column 28, line 51, change "$RC_4$" to --$C_4$--.

Claim 2, column 28, line 60, change "napthyl" to --naphthyl--.

Claim 2, column 29, line 25, change "radial" to --radical--.

Claim 2, column 29, line 26, change "N" to -n--.

Claim 3, column 30, line 3, after "phenyl" insert --,--.

Claim 3, column 30, line 11, change "dimethycyclohexylsilyl" to --"dimethylcyclohexylsilyl--.

Claim 3, column 30, line 21, change "x" to --X--.

Claim 3, column 30, line 22, change "napthyl" to --naphthyl--.

Claim 3, column 30, line 23, change "napthyl" to --naphthyl--.

UNITED STATES PATENT AND TRADEMARK OFFICE
CERTIFICATE OF CORRECTION

PATENT NO. : 5,011,827
DATED : April 30, 1991
INVENTOR(S) : Gerhard Kretzschmar et al.

It is certified that error appears in the above-identified patent and that said Letters Patent is hereby corrected as shown below:

Claim 3, column 30, line 24, change "$c_4$" to --$C_4$--.

Claim 3, column 30, line 45, change "C=X" to -->C=X--.

Claim 3, column 30, line 55, change "$Ch_2$" to --$CH_2$--.

Claim 3, column 31, line 13, change "radial" to --radical--.

Claim 3, column 31, line 14, change "note" to --not--.

Claim 3, column 31, line 19, change "$R^1$," to --$R^{1'}$--.

Claim 3, column 31, line 25, change "$R^1$," to --$R^{1'}$--.

Claim 4, column 31, line 41, change "$C_1$-$C_{15}$-alkenyl" to --$C_1$-$C_{15}$-alkyl, $C_2$-$C_{15}$-alkenyl--.

Claim 4, column 31, line 47, change "$c_4$" to --$C_4$--.

Claim 4, column 31, line 67, change "napthyl" to --naphthyl--.

UNITED STATES PATENT AND TRADEMARK OFFICE
CERTIFICATE OF CORRECTION

PATENT NO. : 5,011,827
DATED : April 30, 1991
INVENTOR(S) : Gerhard Kretzschmar et al.

It is certified that error appears in the above-identified patent and that said Letters Patent is hereby corrected as shown below:

Claim 4, column 31, line 68, change "napthyl" to --naphthyl--.

Claim 4, column 32, line 3, before "denotes" insert --Z--.

Claim 4, column 32, line 4, change "$(CH_2)$" to --$(CH_2)_n$--.

Claim 4, column 32, line 27, change "$\geq C$" to -->C--.

Claim 4, column 32, line 51, delete "13".

Claim 4, column 32, line 58, change "note" to --not--.

Claim 5, column 33, line 2, after "or" change "IV" to --IV'--.

UNITED STATES PATENT AND TRADEMARK OFFICE
CERTIFICATE OF CORRECTION

PATENT NO. : 5,011,827

DATED : April 30, 1991

INVENTOR(S) : Gerhard Kretzschmar et al.

It is certified that error appears in the above-identified patent and that said Letters Patent is hereby corrected as shown below:

Claim 5, column 33, lines 13 and 14, change "β-trimethylsily ethoxymethyl" to --β-trimethylsilylethoxymethyl--.

Claim 5, column 33, line 15, change "dimethycyclohexylsilyl" to --dimethylcyclohexylsilyl--.

Claim 5, column 33, line 30, change "$C_2$" to --$C_1$--.

Claim 5, column 34, line 15, change "C=X" to -->C=X--.

Claim 5, column 34, line 17, change "note" to --not--.

Claim 6, column 34, line 33, delete "are which"

Claim 6, column 34, line 37, change "denotes" to --denote--.

UNITED STATES PATENT AND TRADEMARK OFFICE
CERTIFICATE OF CORRECTION

PATENT NO. : 5,011,827
DATED : April 30, 1991
INVENTOR(S) : Gerhard Kretzschmar et al It is certified that error appears in the above-indentified patent and that said Letters Patent is hereby corrected as shown below:

Claim 6, column 34, line 40, change "dimethycyclohexylsilyl" to --dimethylcyclohexylsilyl--.

Claim 6, column 34, line 50, change "x" to --X--.

Claim 6, column 34, line 51, change "napthyl" to --naphthyl--.

Claim 6, column 34, line 52, change "napthyl" to --naphthyl--.

Claim 6, column 35, line 5, change "C=X" to -->C=X--.

Claim 6, column 36, line 13, change "note" to --not--.

Signed and Sealed this

First Day of February, 1994

Attest:

BRUCE LEHMAN

Attesting Officer

Commissioner of Patents and Trademarks